United States Patent [19]

Campbell

[11] Patent Number: 4,557,867

[45] Date of Patent: Dec. 10, 1985

[54] 11β-DIFLUOROMETHYL AND (E)- AND (Z)-11-FLUOROMETHYLENE STERIODS

[75] Inventor: J. Allan Campbell, Kalamazoo, Mich.

[73] Assignee: The Upjohn Company, Kalamazoo, Mich.

[21] Appl. No.: 639,285

[22] Filed: Aug. 8, 1984

Related U.S. Application Data

[63] Continuation-in-part of Ser. No. 573,787, Jan. 25, 1984, abandoned, which is a continuation-in-part of Ser. No. 561,605, Dec. 14, 1983, abandoned.

[51] Int. Cl.$^4$ .............................................. C07J 33/00
[52] U.S. Cl. ........................ 260/239.5; 260/239.55 C; 260/397.3; 260/397.45; 260/397.5

[58] Field of Search ............. 260/397.45, 239.5, 397.3, 260/397.5, 239.55 C

[56] References Cited

U.S. PATENT DOCUMENTS 4,277,468 7/1981 Hofmeister et al. ........... 260/397.45

Primary Examiner—Elbert L. Roberts
Attorney, Agent, or Firm—Bruce Stein

[57] ABSTRACT

Known reactions are arranged in a novel manner to produce 11β-difluoromethyl and (E)- and (Z)-11-fluoromethylene 19-norandrostenediones and 19-nor-13β-ethylandrostenediones which are useful as contraceptive agents.

12 Claims, No Drawings

11β-DIFLUOROMETHYL AND (E)- AND (Z)-11-FLUOROMETHYLENE STERIODS

BACKGROUND OF THE INVENTION

The present application is a continuation-in-part of co-pending application Ser. No. 573,787, filed Jan. 25, 1984 which was a continuation-in-part of U.S. patent application Ser. No. 561,605 filed Dec. 14, 1983, both now abandoned.

The process of transforming a keto steroid to the corresponding steroid with an aldehyde group attached to what was the carbonyl carbon atom of the ketone is known to those skilled in the art. See, for example C. Byon et al. in J. Org. Chem. 45, 4404 (1980) and references therein, Chem. Abst. 85, 124237 g and East German Patent No. 117,673. However, those references refer to transformation of a 17-keto steroid to the corresponding steroid with an aldehyde group at $C_{17}$ whereas the present invention involves an aldehyde at $C_{11}$.

11β-Formyl-19-norandrostenediones (11β-formylestrones) are known. See, U.S. Pat. No. 4,292,251, Example XI, in column 15, lines 12–14. The compound described is a 3,17-bisethylene ketal.

Difluoromethyl steroids are known with the difluoro substituent at positions $C_{1\alpha}$ (U.S. Pat. No. 3,371,087), $C_2$ (U.S. Pat. No. 3,297,728), $C_4$ (J. Am. Chem. Soc. 104, 4729 (1982)), $C_6$ (J. Org. Chem. 27, 4086 (1962), U.S. Pat. Nos. 3,297,728, 3,328,431, 4,172,132, 4,185,101 and French Patent No. 1,561,908), $C_{7\alpha}$ (Tetrahedron 25, 1219 (1969) and U.S. Pat. Nos. 3,357,975, 3,461,118, 3,357,973, 3,565,918, 3,472,882, 3,338,928, 3,591,582 and 3,453,295), $C_9$ (U.S. Pat. No. 3,409,610), $C_{10}$ (Steroids 39,325 (1982), Biochemistry 21, 2773 (1982) and J. Org. Chem. 45, 2201 (1980)), $C_{13}$ (Ger. Offen. No. 2,533,496, European Patent application 5,758, Can. J. Chem. 58, 2592 (1980) and Swiss Patents 606,093, 606,094 and 616,433), $C_{16}$ (U.S. Pat. Nos. 3,705,182, and 4,242,334) $C_{17\alpha}$ (U.S. Pat. Nos. 3,376,291, 3,370,072 and 3,376,323) and $C_{17\beta}$ (U.S. Pat. No. 4,416,822). No references were found which had any difluoromethyl substitution at $C_{11}$.

Steroids containing a fluoromethylene group (=CHF) are known. These steroids contain the fluoromethylene group only at $C_{16}$ (Ger. Offen. 1,906,586, 1,230,798 and 1,213,402, Belgium Patent Nos. 670,672 and 618,731, Neth. application Nos. 6,500,433 and 295,201, U.S. Pat. Nos. 3,065,239, 3,932,388, 4,124,707, 4,201,778 and 4,267,173, Ber. 95, 2110 (1962) and S. Africa Patent No. 7,000,537) and at $C_{17}$ (Synthesis (2), 75 (1969)). The known fluoromethylene steroids differ from those of the present invention in important ways. The known fluoromethylene steroids are pregnanes (progesterones and corticoids) while the steroids of the present invention do not have the 20-keto-pregnane side chain. Additionally, the known fluoromethylene steroids have a methyl group at $C_{10}$ while the steroids of the present invention are 19-norandrostenediones (estranes) which have a hydrogen atom rather than a methyl group at $C_{10}$. Further, the fluoromethylene steroids of the present invention have the fluoromethylene group at $C_{11}$ while one reference discloses $C_{17}$-fluoromethylene steroids and all the remaining references disclose $C_{16}$-fluoromethylene steroids.

Aldehydes can be transformed to the corresponding difluoromethyl compound by reaction with selenium tetrafluoride, see Olah et al., J. Am. Chem. Soc. 96, 925 (1974), with sulfur tetrafluoride, see Martin and Kagan, J. Org. Chem. 27, 3164 (1962), or with diethylaminosulfur trifluoride, see Fieser and Fieser, Reagents for Organic Synthesis, Wiley Interscience, Vol. 6, p. 183 and Vol. 8, p. 166.

The transformation of 3-ethanedithiol ketal steroids to the corresponding 3-deoxy steroid is known, see, for example Steroids 30, 418 (1977).

11β-Alkylated-$\Delta^{4,9}$-dien-3-ones are known, see, for example, U.S. Pat. No. 4,233,296.

11β-Substituted hetero atom containing steroids which are anti-progestins and are anti-fertility agents are known, see, for example U.S. Pat. No. 4,386,085.

13β-Ethyl-19-nor steroids are known, but not with difluoromethyl or (E) or (Z) fluoromethylene substitution, see U.S. Pat. No. 4,031,074.

SUMMARY OF THE INVENTION

Disclosed are 11β-formyl-19-nor-androstenedione (I), 11β-difluoromethyl-17-keto (II) and (E)-11-fluoromethylene-17-keto (III) steroids. Further disclosed are $C_3$ protected (IV and IV'), 3-unsubstituted (VII and VII'), $\Delta^4$-3-keto (VIII and VIII'), 3-unsubstituted-17-keto (XII and XII'), $\Delta^{5(10)}$-3-keto (XVII and XVII') and $\Delta^{4,9}$-3-keto (XVIII and XVIII') 11β-difluoromethyl and (E)-11-fluoromethylene steroids, respectively.

Also disclosed are the corresponding (Z)-11-difluoromethylene steroids (Z, IV″, VII″, VIII″, XII″, XVII″ and XVIII″).

Further disclosed are the corresponding 13β-ethyl steroids with 11β-difluoromethyl, (E)-11-fluoromethylene and (Z)-11-fluoromethylene substitution (II-Et, III-Et, Z-Et, IV-Et, XII-Et, VII-Et, VIII-Et, XVII-Et, and XVIII-Et).

Also disclosed are the 11-substituted estrone, 11-substituted estradiol, 3-acyloxy and 3β-hydroxy steroids (XIX, XX, XXI, XXII, XIX-Et, XX-Et, XXI-Et and XXII-Et).

DETAILED DESCRIPTION OF THE INVENTION

The 11-hydroxy-19-norandrostenediones (A) are known to those skilled in the art or can be readily prepared from known steroids by methods well known to those skilled in the art. The 11-hydroxy-19-norandrostenediones (A) are oxidized to the corresponding 11-keto-19-norandrostenedione (B) by methods well known to those skilled in the art using such reagents as chromium trioxide, N-bromoacetamide in pyridine or lead tetra acetate, see Steroid Reactions, edited by C. Djerassi, Holden-Day, Inc., San Francisco, 1963, Chapter 2. Either 11α- or 11β-hydroxy steroids may be used as both produce the same 11-keto compound (B).

The 11-keto-19-norandrostenediones (B) are 3,11,17-triones and therefore preferably have the 3 and 17-keto functionality protected prior to further reaction at $C_{11}$. The selective protection of carbonyl groups is well known to those skilled in the art, see Steroid Reactions, supra, Chapter 1. It is preferred that the 3 and 17-keto functionality be protected as the 3,17-bisethylene glycol ketal to produce the protected 11-keto steroid (C).

The protected 11-keto steroid (C) is then converted to a 11-methoxymethylene steroid (D) by a Wittig reaction with methoxymethyltriphenylphosphonium chloride, see Preparation 3 and 3'. The reaction of the protected 11-keto steroid (C) with the methoxymethyltriphenylphosphonium chloride must be performed under strictly dry conditions in an inert atmosphere (preferably dry nitrogen). The phosphonium salt is dried under reduced pressure at about 60° for about 20 hr. The equipment is dried at about 110° for at least 24 hr. The organic solvents such as toluene, benzene, diethyl ether or THF should be from a freshly opened bottle or dried and freshly distilled.

The 11-methoxymethylene steroid (D) is converted to the corresponding 11β-formyl steroid (I) in which the protecting groups at $C_3$ and $C_{17}$ have been removed by reaction with an acid. Inorganic as well as organic acids are operable, but inorganic acids such as hydrochloric, sulfuric, phosphoric are preferred. Acetic, trifluoroacetic, benzoic, p-fluorobenzoic, p-methylbenzoic, nitrobenzoic (o, m and p-) acids are all operable. The reaction is preferably conducted under a nitrogen atmosphere at 20°–25° though higher and lower temperatures are operable.

The 11β-formyl steroid (I) is transformed into the corresponding 11β-difluoromethyl (II), (E)-fluoromethylene (III) and (Z)-11-fluoromethylene steroid (Z) by reaction with a fluorinating agent. The fluorinating agents include, for example diethylaminosulfur trifluoride (DAST), sulfur tetrafluoride catalyzed with hydrogen fluoride and selenium tetrafluoride as is well known to those skilled in the art. DAST is the preferred fluorinating agent. The 11β-formyl (I) starting material is dissolved in an appropriate organic solvent such as methylene chloride, toluene, carbon tetrachloride, chloroform, acetonitrile, pyridine, or mixtures thereof. The mixture is degassed and placed under an inert atmosphere, preferably nitrogen. The fluorinating agent is added. The mixture is stirred at 10°–70°, preferably 20°–25° until the reaction is complete (as measured by TLC). Additional fluorinating agent may have to be added if necessary. The reaction may take 2–96 hr depending on temperature, fluorinating agent, the particular 11β-formyl compound, solvent(s) etc. When the reaction is complete water and ice and an organic solvent are added. The organic layer is separated, washed, dried and concentrated to give a solid. The solid is chromatographed on a silica gel column. The appropriate fractions are pooled and concentrated to give the 11β-difluoromethyl steroid (II), the (E)-11-fluoromethylene steroid (III) and the (Z)-11-fluoromethylene steroid (Z) and further purified as necessary by crystallization. For a good discussion of the nomenclature (E and Z) regarding the cis/trans stereochemistry of double bonded compound see J. Chem. Documentation 8, 30 (1968).

In the fluorinating reaction both the 11β-difluoromethyl (II), (E)-11-fluoromethylene (III) and (Z)-11-fluoromethylene products (Z) are produced, the ratio of which will vary depending on which solvent is used. For example, if acetonitrile with a little water is used the predominate product is the (E)-11-fluoromethylene steroid (III). The (E) isomer is always produced in greater amounts than the corresponding (Z) isomer. With acetonitrile, while the (E) isomer still predominates, the (Z) isomer is produced in a higher ratio than with other solvents and it is produced to the extent that it can be isolated.

The 11β-difluoromethyl steroid (II), and the (E)-11-fluoromethylene steroid (III) are both 17-keto steroids which for optimum pharmacological activity are converted to the corresponding 17β-hydroxy-17α-substituted compounds (VII, VIII, XVII, XVIII, VII', VIII', XVII' and XVIII' respectively). Prior to converting the 17-keto group to the desired 17β-hydroxy-17α-substituent, the 3-keto group must be protected. It can be protected as an enol ether, enamine, ketal or thio ketal as is well known to those skilled in the art. See, Steroid Reactions, supra, Chapter 1. The steroids of the present invention are 19-nor or estrones and protection of the $C_3$ ketone as an enol ether, enamine or ketal results in a mixture of $\Delta^4$, $\Delta^5$ and $\Delta^{5(10)}$ isomers of the $C_3$ protected 11β-difluoromethyl (II), and (E)-11-fluoromethylene steroids (III). The thio ether protecting group is preferred with the 11β-difluoromethyl series because it is produced selectively at $C_3$ in high yield. The enol ether, enamine and ketal $C_3$ protecting groups are operable, but are produced in low yield and are difficult to purify because of the double bond isomers $\Delta^5$ and $\Delta^{5(10)}$. The thio ketal products are obtained pure from the reaction mixture. Therefore, the thio ketal is the preferred protecting group when producing the $C_3$ protected 11β-difluoromethyl and (E)-11-fluoromethylene steroids (IV and IV' respectively). Enamines are good protecting groups because they form selectively at $C_3$. When the protecting group is an enamine, it is preferred that it be the pyrrolidine enamine. With the E and Z isomers in the fluoromethylene series (IV' and IV''), it is preferred that the $C_3$ protecting group be an enamine.

The $C_3$ protected 11β-difluoromethyl, (E)-11-fluoromethylene steroids (IV and IV') are then reacted with the appropriate reagent, as is well known to those skilled in the art, to produce the corresponding 17β-hydroxy- 11β-difluoromethyl and (E)-11-fluoromethylene steroids (V and V' respectively). For example, to produce 17α-ethynyl-17β-hydroxy- 11β-difluoromethyl or (E)-11-fluoromethylene steroids (V and V' respectively) where $R_{17}$ is an ethynyl group ($-C\equiv CH$), the $C_3$ protected 11β-difluoromethyl or (E)-11-fluoromethylene steroid (IV and IV' respectively) are reacted with acetylene in the usual manner, see Example 4. To produce the 17β-hydroxy-17α-propynyl steroids (V and V') where $R_{17}$ is an alkynyl group such as propynyl ($-C\equiv C-CH_3$) the $C_3$ protected 11β-difluoromethyl or (E)-11-fluoromethylene steroid (IV and IV' respectively) is reacted with the appropriate propynyl Grignard reagent as is well known to those skilled in the art, see Example 6. Similarly, the 17-ketone can be reacted with methyl Grignard reagent and other lower alkyl Grignard reagents to afford the 17α-methyl or lower alkyl derivatives (V and V'). The 17-ketone can also be reduced with agents such as sodium borohydride (in alcohol at 0°) to give the 17β-hydroxy- 11β-difluoromethyl or (E)-11-fluoromethylene steroids (V and V') where $R_{17}$ is a hydrogen atom. The free 17β-hydroxyl group can be esterified or etherified by known procedures.

The 17β-hydroxy- 11β-difluoromethyl and (E)-11-fluoromethylene steroids (V and V') can be converted to the corresponding 17-substituted (ether or ester) 11β-difluoromethyl and (E)-11-fluoromethylene steroid (VI and VI') by methods well known to those skilled in the art for forming ethers and esters. Ethers can be formed by reaction of the 17β-hydroxy steroid (V and V') with an alkyl halide such as methyl iodide in the usual manner, see Example 8, 40 and 42. Likewise, 17β-hydroxy steroids (V and V') can be esterified by reaction with pyridine preferably catalyzed with dimethylaminopyridine and the appropriate anhydride (see Examples 36 and 38).

Both the 17β-hydroxy- 11β-difluoromethyl and (E)-11-fluoromethylene steroids (V and V') and the 17β-substituted- 11β-difluoromethyl and (E)-11-fluoromethylene steroids (VI and VI') can be converted to the corresponding 3-unsubstituted- 11β-difluoromethyl and (E)-11-fluoromethylene steroid (VII and VII') by the process of Examples 10 and 11 respectively. The thiol ketal protecting group at $C_3$ is removed by use of sodium and ammonia. For a more detailed explanation of the removal of the $C_3$ protecting thiol ketal group, see Steroids 30, 481 (1977), in particular page 504. Even though both $\Delta^3$ and $\Delta^4$ 3-unsubstituted 11β-difluoromethyl and (E)-11-fluoromethylene (VII and VII') steroids are produced, only the $\Delta^4$ isomer has sufficient biological activity to be useful for the pharmacological utility disclosed.

The thiol ketal protecting group at $C_3$ may be hydrolyzed off from the 17β-hydroxy (V and V') as well as the 17β-substituted (VI and VI') steroids to produce the corresponding $\Delta^4$-3-keto- 11β-difluoromethyl and (E)-11-fluoromethylene steroids (VIII and VIII') by reaction with methyl iodide, water and acetone. See Examples 5, 7, 9, 33, 35, 37, 39, 41 and 43.

An alternative method of producing the 3-unsubstituted- 11β-difluoromethyl and (E)-11-fluoromethylene steroids (VII and VII') is set forth in Chart E. The process involves starting with the $C_3$-protected-11β-difluoromethyl and (E)-11-fluoromethylene steroids (IV and IV') and protecting the $C_{17}$-ketone functionality as the ketal to produce the 3,17-diprotected- 11β-difluoromethyl and (E)-11-fluoromethylene steroids (IX and IX'), selectively reducing off the $C_3$-thiol ketal protecting group to produce the $C_{17}$-protected- 11β-difluoromethyl and (E)-11-fluoromethylene steroids (X and X'). Here it is useful to protect the steroid at $C_3$ as the thio ketal (to maintain the $\Delta^4$ double bond) and the $C_{17}$ ketone as the ketal so that the $C_3$ protecting group can be selectively eliminated producing the $C_{17}$-protected-11β-difluoromethyl or (E)-11-fluoromethylene steroid (X and X'). In this reaction also produced is the $\Delta^3$-protected- 11β-difluoromethyl and (E)-11-fluoromethylene steroids (XI and XI'). The mixture of the $C_{17}$-protected- (X and X') and $\Delta^3$-protected- (XI and XI') steroids is further reacted, as a mixture, by removal of the $C_{17}$-ketal protecting group by methods well known to those skilled in the art to produce the 3-unsubstituted-17-keto 11β-difluoromethyl and (E)-11-fluoromethylene steroids (XII and XII') as well as the corresponding $\Delta^3$- 11β-difluoromethyl and (E)-11-fluoromethylene steroids (XIII and XIII'). Next the 3-unsubstituted-17-keto- 11β-difluoromethyl and (E)-11-fluoromethylene steroid (XII and XII') is reacted such that the 17-keto group is transformed to the corresponding 17α-substituted-17β-hydroxy functionality to produce the desired 3-unsubstituted-11β-difluoromethyl and (E)-11-fluoromethylene steroid (VII and VII'). The 17β-hydroxy group can then be transformed to the corresponding ether or ester as was described previously. Hence, there are two alternative procedures to produce the 3-unsubstituted 11β-difluoromethyl and (E)-11-fluoromethylene steroids (VII and VII') starting with $C_3$-protected- 11β-difluoromethyl and (E)-11-fluoromethylene steroids (IV and IV' respectively).

Charts F and F' disclose the transformation of 11β-difluoromethyl-17-keto steroid (II) and (E)-11-fluoromethylene-17-keto steroid (III) to the corresponding $\Delta^{5(10)}$-3-keto- 11β-difluoromethyl and (E)-11-fluoromethylene steroids (XVII and XVII') and the $\Delta^{4,9}$-11β-difluoromethyl and (E)-11-fluoromethylene steroids (XVIII and XVIII'). The appropriate 17-keto steroid (II or III) has the $C^3$-ketone protected as the ketal. By using the ketal as a protecting group rather than the thiol ketal, mixtures of the $\Delta^{5(10)}$-isomer (XIV and XIV') and $\Delta^5$-isomer (XV and XV') are produced as previously discussed. The transformation of the 11-keto steroid (B) to the protected 11-keto steroid (C) uses ethylene glycol, p-TSA at reflux for 3–6 hr to produce the 3,17-bis ketal, see Preparation 2 and Example 24. The transformation of the 11β-difluoromethyl-17-keto steroid (II) to the $\Delta^{5(10)}$-17-keto-11β-difluoromethyl steroid (XIV) and $\Delta^5$-17-keto-11β-difluoromethyl steroid (XV) uses only 25% the amount of p-TSA as used in Preparation 2 and Example 24 and the reaction is conducted at 0°–25° to minimize the amount of bis ketal formation, see Example 19. The $\Delta^{5(10)}$-17-keto- 11β-difluoromethyl and (E)-11-fluoromethylene steroids (XIV and XIV') are next reacted as previously described to transform the 17-keto group to appropriate propargyl alcohol at $C_{17}$ to produce the $\Delta^{5(10)}$-$C_3$-protected- 11β-difluoromethyl and (E)-11-fluoromethylene steroid (XVI and XVI'). Upon removal of the $C_3$-ketal protecting group to produce the 3-keto functionality, a $\Delta^{5(10)}$-3-keto- 11β-difluoromethyl or (E)-11-fluoromethylene steroid (XVII and XVII') is formed. The ketal is hydrolyzed without isomerization of the double bond, see Synthesis 63 (1978). The $\Delta^{5(10)}$-3-keto-11β-difluoromethyl or (E)-11-fluoromethylene steroid (XVII and XVII') is converted to the corresponding $\Delta^{4,9}$-diene by bromination, dehydrobromination as described in J. Am. Chem. Soc. 82, 2402 (1960) to obtain the $\Delta^{4,9}$- 11β-difluoromethyl or (E)-11-fluoromethylene steroid (XVIII and XVIII').

Just as the 17-keto 11β-difluoromethyl steroids (II) and the (E)-11-fluoromethylene steroids (III) are converted to the corresponding pharmacologically active 17β-hydroxy-17α-substituted compounds (VII, VII', VIII, VIII', XVII, XVII', XVIII and XVIII') by the processes described above, similarly the 17-keto (Z)-11-fluoromethylene steroid (Z) is converted to the corresponding 17β-hydroxy-17α-substituted pharmacologically active steroids (VII'', VIII'', XVII'' and XVIII'').

The 13β-ethyl steroids (-Et) are produced similarly to the 13β-methyl steroids. A 13β-ethyl 11-hydroxy steroid (A-Et) is oxidized to a 13β-ethyl-11-keto steroid (B-Et) which is then transformed to a protected 13β-ethyl 11-keto steroid (C-Et) which is then transformed to a 13β-ethyl-11-methoxymethylene steroid (D-Et) and ultimately to a 13β-ethyl-11β-formyl steroid (I-Et), see Examples 59 and 60. The 13β-ethyl-11β-formyl steroid (I-Et) is fluorinated to produce a mixture of 13β-ethyl-11β-difluoromethyl (II-Et), 13β-ethyl-(E)-11-fluoromethylene (III-Et) and 13β-ethyl-(Z)-11-fluoromethylene (Z-Et, see Chart B-Et. The 13β-Et 11β-difluoromethyl (II-Et), (E)-11-fluoromethylene (III-Et) and (Z)-11-fluoromethylene (Z-Et) are converted to the corresponding C3-protected form (IV-Et), see Chart C-Et, where $R^{11}$ represents the 11β-difluoromethyl, (E)-11-fluoromethylene and (Z)-11-fluoromethylene group, see Chart D-Et. The 13β-ethyl steroid intermediates (II-Et, III-Et, Z-Et, IV-Et) are transformed to the pharmacologically active 13β-ethyl steroids (VII-Et, VIII-Et, XVII-Et and XVIII-Et) by the same process chemistry as the corresponding 13β-methyl steroids (II, III, Z, IV, IV' and IV''), see Charts D-Et thru I-Et.

The process chemistry of the present invention involves the use of reactions well known to those skilled in the art. These reactions, each well known to those skilled in the art, are arranged in a novel manner to produce the novel compounds of the present invention.

The 11$\beta$-formyl (I), 11$\beta$-difluoromethyl (II, IV and XII) and the (E)-11-fluoromethylene (III, IV' and XII') steroids are intermediates useful in production of the pharmacologically active 11$\beta$-difluoromethyl (VII, VIII, XVII and XVIII) and (E)-11-fluoromethylene (VII', VIII', XVII' and XVIII') steroids.

The (Z)-11-fluoromethylene (Z, IV" and XII") steroids are useful as intermediates in the production of the pharmacologically active (Z)-11-fluoromethylene (VII", VIII", XVII" and XVIII") steroids.

The 13$\beta$-ethyl steroids (II-Et, III-Et, Z-Et, IV-Et and XII-Et) are useful as intermediates in the production of the pharmacologically active 13$\beta$-ethyl (VII-Et, VIII-Et, XVII-Et and XVIII-Et) steroids.

The 11$\beta$-difluoromethyl (II and II-Et), (E)-11-fluoromethylene (III and III-Et) and (Z)-11-fluoromethylene (Z and Z-Et) steroids are converted to the corresponding 11-substituted estrone (XIX and XIX-Et) as is well known to those skilled in the art.

The 11-substituted estrone (XIX and XIX-Et) is transformed to the corresponding 11-substituted estradiol (XX and XX-Et) with a ketone reducing agent as is well known to those skilled in the art. See Steroid Reactions, Carl Djerassi, Holden-Day Inc., San Francisco 1963, Chapter 1. Preferred is sodium borohydride.

The $\Delta^4$-3-keto-11$\beta$-difluoromethyl, $\Delta^4$-3-keto-(E)-11-fluoromethylene and $\Delta^4$-3-keto-(Z)-11-fluoromethylene steroids (VIII, VIII', VIII" and VIII-Et) are transformed to the corresponding 3$\beta$-hydroxy steroid (XXII and XXII-Et) by way of the enol acylate intermediate, the 3-acyloxy steroid (XXI and XXI-Et) is reduced by sodium borohydride in aqueous ethanol as is well known to those skilled in the art.

The 11-substituted estrone (XIX and XIX-Et) are useful both as an intermediate in production of the pharmacologically active 11-substituted estradiol (XX and XX-Et) and also because of its own pharmacological activity.

The 3-acyloxy steroids (XXI and XXI-Et) are useful as intermediates in the production of the pharmacologically active 3$\beta$-hydroxy steroid (XXII and XXII-Et).

The 11$\beta$-difluoromethyl and (E)-11-fluoromethylene steroids (VII, VIII, XVII, XVIII, VII', VIII', XVII' and XVIII' respectively) have progestational, antiprogestational and male and female antifertility activity and therefore are useful for pregnancy salvage and menopausal therapy and as male and female contraceptive agents in humans and other mammals.

The 11$\beta$-difluoromethyl and (E)-11-fluoromethylene steroids (VII, VIII, XVII, XVIII, VII', VIII', XVII' and XVIII' respectively) may be used either individually or in combination with each other.

The 11$\beta$-difluoromethyl and (E)-11-fluoromethylene steroids (VII, VIII, XVII, XVIII, VII', VIII', XVII' and XVIII) which have female progestational activity and are useful in treating pregnancy salavage and menopausal therapy as progestins are those 11$\beta$-difluoromethyl and (E)-11-fluoromethylene steroids (VII, VIII, XVII, XVIII, VII', VIII', XVII' and XVIII) which have similar activity to progesterone in the following tests: DAO (diamine oxidase), McPhail, pregnancy maintenance in castrated laboratory animals as is well known to those skilled in the art, see for DAO Assay, A New Progestational Assay; Uterine Diamine Oxidase, Fertility and Sterility 1976 by M. E. Harris and K. S. Kim; Uterine Diamine Oxidase, a Marker for Progestin Action, by C. H. Spilman, D. C. Beuving and K. K. Bergstrom, *Reproductive Processes and Contraception*, (edited by K. W. Harris), Plenuin Publishing Corp., New York 1981, p. 509–519; for McPhail Assay, J. Physiol. 83, 145 (1935); and for pregnancy maintenance, Proc. Soc. Exper. Biol. & Med. 99, 500 (1958); Recent Progress in Endocrinology of Reproduction by F. J. Saunders and R. L. Elton, Academic Press, 1959, p. 227–254. The 11$\beta$-difluoromethyl and (E)-11-fluoromethylene steroids (VII, VIII, XVII, XVIII, VII', VIII', XVII' and XVIII) useful for treating pregnancy salvage or in menopausal therapy are administered so that the female mammal receives about 0.002 to about 0.50 mg/kg/day or for a 50 kg female, the amount would be about 0.1 to about 25 mg/day, preferably from about 1 to about 5 mg/day.

The 11$\beta$-difluoromethyl and (E)-11-fluoromethylene steroids (VII, VIII, XVII, XVIII, VII', VIII', XVII' and XVIII' respectively) which have either progestational or antiprogestational activity are useful as male and female contraceptive agents and are used to provide reversible contraception for male and female mammals post-puberty which are selected from the group consisting of man, male dog, tom, bull, stallion, ram, boar, male rat and male mouse and their female counterparts.

With regards to the human, there are many instances in which the female cannot take various types of chemical contraceptive agents and does not or cannot use various physical contraceptive devices such as IUD (IUCD) or diaphragm. In addition, many women do not wish to rely on non-prescription (over-the-counter) foams, gels and cream chemical contraceptive agents. Therefore, there are numerous instances in which it would be highly desirable to have a reliable reversible contraceptive agent for men. This is particularly true in view of the fact that the only reversible contraceptive agent for man is a mechanical device (prophylactic) which has the distinct disadvantage of low efficacy. In addition, there is the disadvantage of mechanical devices of having to interrupt intercourse to properly position the device.

The useful warm blooded animals can be divided into two groups—domesticated (dog, tom) and commercial (bull, stallion, ram and boar). The domesticated male animals usually cohabitate with the females. The commercial male animals are usually separated from the females because either it is desired that the particular males not fertilize the females so that artificial insemination may be used, or even if the particular males are well suited to fertilizing the females it may be desired that they not do so at the present time. The use of the methods of the present invention permits one to allow both the domestic and commercial male and females to cohabitate without sterilization of either sex and without unwanted pregnancies and still retain the flexibility of fertilizing the female when desired either with a desired male or by artificial insemination.

With regards to the rodents, the rat and mouse, it is highly desirable of course to be able to eradicate or control the populations of these rodents with the methods of the present invention. These rodents can be controlled and/or eradicated by decreasing the fertility of these rodents by use of the methods of the present invention. This of course would not eliminate the rodents which are present, but only future rodents which these animals might conceive, thereby decreasing future populations of these undesirable animals.

The 11β-difluoromethyl and (E)-11-fluoromethylene steroids (VII, VIII, XVII, XVIII, VII', VIII', XVII' and XVIII) which are useful as male contraceptive agents are those which depress gonadotropins in castrated laboratory animals. See, Fed. Proc. 18, 1057 (1959). The 11β-difluoromethyl steroids (VII, VIII, XVII and XVIII) are administered such that the male mammal receives about 0.01 to about 1.0 mg/kg/day. For a 70 kg male, the amount would be about 0.7 to about 70 mg/day.

The (E)-11-fluoromethylene steroids (VII', VIII', XVII', XVIII') which are useful as male contraceptive agents are administered such that the male mammal receives about 0.001 to about 1.0 mg/kg/day. For a 70 kg male, the amount would be about 0.07 to about 70 mg/day.

The 11β-difluoromethyl steroids (VII, VIII, XVII and XVIII) useful as female contraceptive agents are those 11β-difluoromethyl steroids (VII, VIII, XVII and XVIII) with anti-progestational activity, i.e., those compounds which inhibit the action of progesterone in the following tests: DAO, nuclear translocation, expression of uteroglobin gene, and most importantly interruption of pregnancy in laboratory animals as is well known to those skilled in the art, see for DAO assay supra. Those 11β-difluoromethyl steroids (VII, VIII, XVII and XVIII) are administered such that the female mammal receives about 0.01 to about 1.0 mg/kg/day. For a 50 kg female, the amount would be about 0.5 to about 50 mg/day.

The (E)-11-fluoromethylene steroids (VII', VIII', XVII' and XVIII') which are useful as female contraceptive agents are those (E)-11-fluoromethylene steroids (VII', VIII', XVII' and XVIII') which have anti-progestational activity as identified supra and which are administered such that the female mammal receives about 0.001 to about 1.0 mg/kg/day. For a 50 kg female, the amount would be about 0.05 to about 50 mg/day.

The exact dose of the 11β-difluoromethyl and (E)-11-fluoromethylene steroids (VII, VIII, XVII, XVIII, VII', VIII', XVII' and XVIII' respectively) will depend on the particular compound, the weight, age, and physical condition of the particular patient to be treated.

The 11β-difluoromethyl and (E)-11-fluoromethylene steroids (VII, VIII, XVII, XVIII, VII', VIII', XVII' and XVIII' respectively) contraceptive agents administered by oral, parenteral, in sustained release form, intrauterine, intravaginal means in the appropriate dosage forms.

Oral dosage forms include both solid and liquid. The solid dosage forms include tablets (compressed, tablet triturates, enteric coated, sugar coated, film coated and multiple compressed), capsules (hard and soft gelatin), treats, bait, veterinary premix and animal feed. The liquid oral dosage forms include, for example, aqueous solutions (elixirs and syrups), emulsions, and suspensions. In the parenteral sustained release form, the active ingredient is slowly released over a prolonged period as is well known to those skilled in the art. These preparations are known as sustained release parenteral forms or depo forms.

One method of formulating parenteral depo compositions is to administer the drug dissolved in or suspended in oil. An oleaginous solution or suspension injected intramuscularly provides a depot which slowly releases the drug to tissue fluid and the blood. The oil may be modified by the inclusion of wax or some other water-repellant substance such as aluminum stearate which further reduces the release rate of the therapeutically active ingredient.

An alternative long acting parenteral composition is one where the relatively water-insoluble 11β-difluoromethyl and (E)-11-fluoromethylene steroids (VII, VIII, XVII, XVIII, VII', VIII', XVII' and XVIII' respectively) are suspended in an aqueous medium. The aqueous medium can be modified by the addition of certain hydrocolloids such as gelatin, carboxymethyl cellulose or polyvinylpyrrolidone. The contraceptive steroids of the present invention are quite water-insoluble and those which are crystalline lend themselves very well to this type of formulation.

Long acting parenteral steroidal compositions in oil are well known to those skilled in the art. For example, see testosterone cypionate USP (See Physicians Desk Reference, PDR, 31 edition, 1977, page 1625); nandrolone phenpropionate N.F. (PDR, ibid., page 1138); estradiol cypionate injection USP and testosterone enanthate USP (PDR, ibid., page 1512) which is advertised as having a duration of action of about 4 weeks.

Long acting aqueous parenteral compositions are also well known to those skilled in the art. See British Patent Nos. 705,343 and 731,933. Various long acting aqueous parenteral steroidal preparations are well known to those skilled in the art. See British Patent No. 731,933, Examples 1–4 and methylprednisolone acetate suspension N.F. (PDR, ibid., page 1623) and medroxyprogesterone acetate suspension (PDR, ibid., page 1625).

U.S. Pat. No. 4,038,389 discloses and claims aqueous parenteral compositions containing 200–600 mg/ml of medroxyprogesterone. The usual therapeutic dose of medroxyprogesterone is 2.5–10 mg, see PDR, ibid., page 1648, where the product is marked in oral tablet form at two dose levels, 2.5 and 10.0 mg. The very high dose of medroxyprogesterone disclosed in U.S. Pat. No. 4,038,389 is obviously because it is in long acting (depot) form intended to have a duration of action of many weeks. See The Journal of Reproductive Physiology 13, 113 (1974), where the composition claimed in U.S. Pat. No. 4,038,389 had a duration of action of at least 3 months in preventing pregnancy.

In 1977 five papers appeared in the journal Contraception, Vol. 15, at pages 627, 635, 649, 669 and 679, which show that testosterone can be administered parenterally in a form which will provide effective amounts of testosterone for a period of at least one month.

Therefore, the technology is known to those skilled in the art to formulate the 11β-difluoromethyl and (E)-11-fluoromethylene contraceptive steroids of the present invention into depot or long acting parenteral preparations. The depot parenteral preparations should release the male contraceptive steroid at the rate of about 0.01 to about 1.0 mg/kg/day.

An alternative pharmaceutical composition to deliver the 11β-difluoromethyl and (E)-11-fluoromethylene contraceptive steroids to the desired animal at a controlled rate over a long period of time is the implant. The technology for formulating the proper implants is well known to those skilled in the art. The J. of Animal Science 35, 251 (1972), in an article by M. L. Ogilvie, describes a polyurethane implant containing melengesterol acetate which was used in heifers for over four months. John B. Herrick in Animal Nutrition and Health, April 1977, at page 23, describes a number of growth promotants for beef cattle. Many of these growth promotants are steroids, including testosterone, and are administered by implants. L. L. Ewing et al., in Contraception 13, 583 (1976), describes a method of decreasing sperm counts in male rhesus monkeys by administering testosterone via subdermal dimethylpolysiloxane implants. The implants were left in for 70 days, and the results demonstrate the satisfactory nature of this method. W. E. Johansson et al., in Contraception 13, 287 (1976), describes using dimethylpolysiloxane implants containing a steroid in women for over four months. Further, U.S. Pat. No. 3,896,819 discloses a drug delivery device for administering a drug at a controlled rate for a prolonged period of time. The drug delivery device can be used as an implant, see column 6, starting at line 55. This implant is useful with steroids such as methyltestosterone, see column 19, starting at line 24. The implant should release the 11$\beta$-difluoromethyl and (E)-11-fluoromethylene contraceptive steroids of the present invention at the rate of about 0.01 to about 1.0 mg/kg/day.

The pharmaceutically therapeutically active 11$\beta$-difluoromethyl and (E)-11-fluoromethylene contraceptive steroids of the present invention are administered orally or parenterally in unit-dosage forms or multiple-dosage forms. Unit-dose forms refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampuls and syringes (parenteral) and individually packaged tablet or capsule (oral-solid). Unit-dose forms may be administered in fractions or multiples thereof. A multiple-dose form is a plurality of identical unit-dosage forms packaged in a single container to be administered in segregated unit-dose form. Examples of multiple-dose forms include vials (parenteral) and bottles of tablets of capsules (oral-solid). Hence, multiple dose forms is a multiple of unit-doses which are not segregated in packaging. The specifications for the unit-dosage form and the multiple-dosage form are dictated by and directly dependent on (a) the unique characteristics of the particular 11$\beta$-difluoromethyl and (E)-11-fluoromethylene steroid (IV, VIII, XI or XII) and the particular therapeutic effect to be achieved and (b) the limitations inherent in the art of compounding such a therapeutically active compound for reversible contraception.

The individual oral solid pharmaceutical dosage forms, tablets and capsules, are packaged individually (unit dose) or in quantity (multiple dose containers), for examples bottles of 50, 100, 500, 1,000 or 5,000. The amount of the 11$\beta$-difluoromethyl and (E)-11-fluoromethylene steroid (VII, VIII, XVII, XVIII, VII', VIII', XVII' and XVIII' respectively) per dosage unit (tablet or capsule) is adjusted so that the tablet or capsule, a fraction or multiple thereof, provides the patient with an effective amount. It is preferred that each tablet or capsule contain 1-250 mg of the 11$\beta$-difluoromethyl and (E)-11-fluoromethylene steroids (VII, VIII, XVII, XVIII, VII', VIII', XVII' and XVII' and XVIII' respectively). The exact dosage depends on the particular compound, the age, weight, physical condition and particular patient or animal, as is known to those skilled in the art. Tablets and capsules are given in sufficient number and frequency to obtain the desired contraceptive effect.

U.S. Pat. No. 4,252,798 describes various dosage forms useful for a male contraceptive agent. While that patent describes dosage forms useful for a male contraceptive agent, those forms are equally applicable to the female contraceptive steroids of the present invention. U.S. Pat. No. 4,252,798 has a thorough discussion of sustained release tablets and capsules, tablet formulations used to treat dogs, cats and rabbits, treats, bait, liquid dosage forms, veterinary premixes, and animal feed compositions.

Following cessation of administration of the 11$\beta$-difluoromethyl and (E)-11-fluoromethylene steroids (VII, VIII, XVII, XVIII, VII', VIII', XVII' and XVIII' respectively), or at the end of the metering out of the parenteral sustained release formulation, contraception will be maintained only for a very short period, and gradually, the animal's ability to fertilize or be fertilized returns to normal.

The 11$\beta$-difluoromethyl and (E)-11-fluoromethylene steroids (VII, VIII, XVII, XVIII, VII', VIII', XVII' and XVIII') are also useful for treating benign prostatic hypertrophy (BPH) in humans. The steroids are administered in the dosage forms described above and in the dosages previously described.

Biological information in the form of progesterone receptor relative binding affinity data determined according to the procedure of D. Philibert et al, Endocrinology 101, 1850 (1977) set forth in TABLE 1 discloses the 11$\beta$-difluoromethyl and (E)-11-fluoromethylene steroids to be useful as progestins.

Biological information in the form of DAO assay data set forth in TABLE 1 discloses the antiprogestational activity of the 11$\beta$-difluoromethyl and (E)-11-fluoromethylene steroids. DAO assay data can be determined according to the procedure of C. H. Spilman et al. Reproductive Processes and Contraception Plenum Publishing Cop., 1981, p 5030.

The (Z)-11-fluoromethylene steroids (VII'', VIII'', XVII'' and XVIII'') are useful in the same way and in the same manner as the corresponding 11$\beta$-difluoromethyl and (E)-11-fluoromethylene steroids (VII, VIII, XVII, XVIII, VII', VIII', XVII' and XVIII').

The 13$\beta$-ethyl 11$\beta$-difluoromethyl, (E)-11-fluoromethylene and (Z)-11-fluoromethylene steroids (VII-Et, VIII-Et, XVII-Et and XVIII-Et) are useful in the same way and in the same manner as the corresponding 13$\beta$-methyl steroids (VII, VIII, XVII, XVIII, VII', VIII', XVII', XVIII', VII'', VIII'', XVII'' and XVIII'').

The 11-substituted estradiol (XX), 3$\beta$-hydroxy (XXII), 13$\beta$-11-substituted estradiol (XX-Et) and 13$\beta$-11-substituted-3$\beta$-hydroxy (XXII-Et) steroids are useful in the same way and same manner as the corresponding 11$\beta$-difluoromethyl, (E)-11-fluoromethylene and (2)-11-fluoromethylene steroids (VII, VIII, XVII, XVIII, VII', VIII', XVII', XVIII', VII'', VIII'', XVII'' and XVIII'').

DEFINITIONS

The definitions and explanations below are for the terms as used throughout the entire patent application including both the specification and the claims.

All temperatures are in degrees Centigrade.
TLC refers to thin-layer chromatography.
THF refers to tetrahydrofuran.

SSB refers to an isomeric mixture of hexanes.

p-TSA refers to p-toluenesulfonic acid monohydrate.

Saline refers to an aqueous saturated sodium chloride solution.

IR refers to infrared spectroscopy.

UV refers to ultraviolet spectroscopy.

NMR refers to nuclear (proton) magnetic resonance spectroscopy, chemical shifts are reported in ppm ($\delta$) downfield from TMS.

TMS refers to tetramethylsilane.

$[\alpha]_D^{25}$ refers to the angle of rotation of plant polarized light (specific optical rotation) at 25° with the sodium D line (5893A).

MS refers to mass spectrometry expressed as m/e or mass/change unit.

When solvent pairs are used, the ratios of solvents used are volume/volume (v/v).

Ether refers to diethyl ether.

Alcohol refers to ethyl alcohol.

Androstenedione refers to androst-4-ene-3,17-dione.

When the term "alkyl of __ through __ carbon atoms" is used, it means and includes isomers thereof where such exist.

$R_3$ is alkyl of 1 thru 5 carbon atoms or phenyl.

$R_3A$ is a

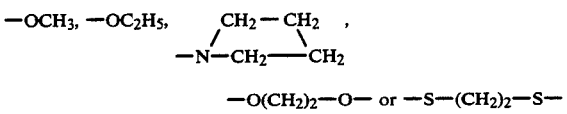

group.

$R_6$ is a hydrogen atom or methyl group with the proviso that when $R_6$ is methyl group, $R_7$ is a hydrogen atom.

$R_7$ is hydrogen atom or methyl group with the proviso that when $R_7$ is a methyl group, $R_6$ is a hydrogen atom.

$R_{11}$ refers to a difluoromethyl, (E)-fluoromethylene or (Z)-fluoromethylene group.

$\sim$ indicates that the attached group can be in either the $\alpha$ or $\beta$ configuration.

$R_{17}$ is a hydrogen atom, alkyl of 1 through 4 carbon atoms, —C≡C—$R_{17A}$, —CH=CH—$R_{17B}$.

$R_{17A}$ is a hydrogen atom, methyl or ethyl group or trifluoromethyl.

$R_{17B}$ is a hydrogen atom, methyl or ethyl group or —CH=$CH_2$ group.

$R_{17\beta}$ is alkyl of 1 through 4 carbon atoms and —CO—$R_{17C}$.

$R_{17C}$ is alkyl of 1 through 6 carbon atoms, cyclopentylethyl and phenyl.

$R_{17\beta'}$ is a hydrogen atom or $R_{17\beta}$.

DAST refers to diethylaminosulfur trifluoride.

Antiprogestational or antiprogestin refers to any compound that will interfere or inhibit the action of progesterone at any progesterone target tissue.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1

Estr-4-ene-3,11,17-trione (B)

To a degassed stirred solution of 11α-hydroxy-19-norandrostenedione in acetic acid (225 ml) is added in order a solution of manganese sulfate (2.25 g) in water (130 ml), a solution of chromium trioxide (15 g) in water (15 ml) and concentrated sulfuric acid (14 ml). The sulfuric acid is added dropwise (over 15 min) keeping the temperature near 15° by cooling in an ice bath. The cooling bath is removed after 1.5 hours when TLC shows the reaction to be complete. The mixture is cooled to 15° and sodium hydroxide (50%, 124 ml) diluted with water (147 ml) is added dropwise. Finally a solution of sodium bisulfite in water (7.7 g in 67.5 ml) is added. The precipitate is filtered, washed well with water and dried under reduced pressure to give the title compound, mp 204°-209°; UV (ethyl alcohol) $\lambda_{max}$=239 nm ($\epsilon$=16,000); IR (mull) 1742, 1711, 1674 and 1617 cm$^{-1}$; MS (m/e)=286, 268, 258 and 244; NMR (CDCl$_3$)=0.89 and 585 $\delta$.

Preparation 2

Estr-5-ene-3,11,17-trione 3,17-bisethylene glycol ketal (C)

A mixture of estr-4-ene-3,11,17-trione (B, Preparation 1, 41 g) in methylene chloride (543 ml), ethylene glycol (308 ml), triethylortho formate (138 ml) is degassed followed by the addition of p-TSA (410 mg). The mixture is refluxed for 6 hours. The mixture is cooled and diluted with bicarbonate solution. The methylene chloride layer is separated, washed several times with water, dried and concentrated to foam. The foam is triturated several times with diethyl ether-SSB and dried to give the title compound, NMR (CDCl$_3$) 0.85, 3.50 and 5.43 $\delta$; MS (m/e) 374, 356, 346 and 99.

Preparation 3

11-(Methoxymethylene)-estr-5-ene-3,17-dione 3,17-bisethylene glycol ketal (D)

Note. Preparation 3 is run under very dry conditions under nitrogen. The phosphonium salt is dried under reduced pressure at 60° for 20 hours and the equipment is dried at 110° for at least 24 hours. The toluene is from a freshly opened bottle.

Powdered potassium t-butoxide is added to a slurry estr-5-ene-3,11,17-trione 3,17-bisethyleneglycol ketal (C, Preparation 2, 22.9 g) and methoxymethyltriphenylphosphonium chloride (75 g) in toluene (1,527 ml). After 24 hours TLC shows the reaction to be about half completed. Methoxymethyltriphenylphosphonium chloride (75 g) and potassium t-butoxide (25 g) are added. 24 hours later a third portion of the phosphonium salt and potassium t-butoxide are added. 24 hours later water is added to the reaction mixture. The organic phase is separated and washed twice with methanol-water (70/30, 500 ml). The toluene phase is concentrated and the product chromatographed over a silica gel column (900 g). The appropriate fractions are pooled and triturated with SSB to give the title compound, NMR (CDCl$_3$) 0.78, 3.55, 3.97, 3.91, 5.45 and 5.85 $\delta$.

Preparation 3'

11-(Methoxymethylene)-estr-5-ene-3,17-dione 3,17-bisethylene glycol ketal (D)

Note. The precautions of Preparation 3 should be observed in forming Preparation 3'.

Estr-5-ene-3,11,17-trione 3,17-bisethyleneglycol ketal (C, Preparation 2, 121 g dry), methoxymethyltriphenylphosphonium chloride (375 g dried under vacuum) and fresh toluene (8068 ml) are degassed under vacuum and nitrogen. Dry powdered potassium t-butoxide (125 g) is added with stirring. After 24 hours additional phosphonium chloride (375 g) and potassium t-butoxide (125 g) is added and the mixture stirred for an additional 24 hours. Water is added and the mixture extracted with toluene. The aqueous phase is back-extracted with 2 portions of diethyl ether. The toluene phase is washed 4 times with 1 liter portions of a 60% methanol/water mixture and once with water. The diethyl ether back-extracts are added to the toluene phase and hydrogen peroxide (30%, 200 ml) is added and the mixture stirred for one hour. TLC shows the triphenyl phosphine is converted to triphenyl phosphine oxide. The organic phases are dried and concentrated under reduced pressure and then triturated 6 times with 200 ml amounts of a 60% methanol/water mixture. TLC shows only product which is dried to give the title compound, NMR (CDCl$_3$) 0.84, 3.61, 3.97, 4.02 5.53 and 5.95 $\delta$; mp 195°–199°.

EXAMPLE 1

11$\beta$-Formylestr-4-ene-3,17-dione (I)

A mixture of 11-(methoxymethylene)-estr-5-ene-3,17-dione 3,17-bisethylene glycol (D, Preparation 3, 12 g) in acetone (600 ml) is degassed under reduced pressure and hydrochloric acid (6N, 3.6 ml) is added under a nitrogen atmosphere. The mixture is stirred and after 4 hours water is added and the product extracted with methylene chloride. The extract is washed, dried over sodium sulfate, concentrated under reduced pressure to a solid residue and crystallized from diethyl ether to give the title compound, NMR (CDCl$_3$) 0.82, 5.87, and 9.85 $\delta$; UV (ethyl alcohol) $\lambda_{max}$=239 nm ($\epsilon$=16,650); IR (mull) 1734, 1715, 1664, and 1620 cm$^{-1}$; MS (m/e) 300, 282, 272 and 110.

EXAMPLE 1'

11$\beta$-Formylestr-4-ene-3,17-dione (I)

Hydrochloric acid (6N, 10 ml) is added to a deoxygenated slurry of 11-(methoxymethylene)-estr-5-ene-3,17-dione 3,17-bisethylene glycol ketal (D, Preparation 3', 100 g) in acetone (2.5 liters). The mixture is stirred and after 4 hours the reaction is complete as measured by TLC. Sodium bicarbonate (5.54 g) and water (500 ml) are added. The acetone is removed under reduced pressure with warming. Water (200 ml) is added and the precipitated product is collected by filtration, washed several times with a total of 125 ml of absolute diethyl ether, the solids are dried at 20°–25° under reduced pressure for 48 hours to give the title compound, NMR (CDCl$_3$) 0.82, 5.91, and 10.0 $\delta$.

EXAMPLE 2

11$\beta$-Difluoromethylestr-4-ene-3,17-dione (II) and (E)-11-(Fluoromethylene)estr-4-ene-3,17-dione (III)

Diethylaminosulfur trifluoride (DAST 14.5 ml) is added to a degassed mixture of 11$\beta$-formylestr-4-ene-3,17-dione (I, Example 1, 6.5 g) in methylene chloride (361 ml) under a nitrogen atmosphere. After 24 hours additional DAST (2 ml) is added and after another 24 hours water and ice are added to the reaction mixture. The methylene chloride phase is separated, washed with water, dried over sodium sulfate and concentrated to dryness. The solid is chromatographed over silica gel, the appropriate fractions are pooled and concentrated to a solid and recrystallized from acetone to give 11$\beta$-difluoromethylestr-4-ene-3,17-dione (II), mp 149°–151°; NMR (CDCl$_3$) 0.95, 5.86, and 6.02 $\delta$; UV (ethyl alcohol) $\lambda_{max}$=237 nm ($\epsilon$=17,350); IR (mull) 1741, 1662 and 1619 cm$^{-1}$; MS (m/e)=322, 304 and 292. Additional fractions are collected and pooled and concentrated to give (E)-11-(fluoromethylene)estr-4-ene-3,17-dione (III), mp 208°–212°; NMR (CDCl$_3$) 0.90, 5.88 and 6.58 $\delta$; UV (ethyl alcohol) $\lambda_{max}$=238 nm ($\epsilon$=16,500); IR (mull) 1737, 1664 and 1610 cm$^{-1}$; MS (m/e) 302, 282, 260 and 193.

EXAMPLE 2'

11$\beta$-Difluoromethylestr-4-ene-3,17-dione (II) and (E)-11-(Fluoromethylene)-estr-4-ene-3,17-dione (III)

DAST (50 ml) is added with stirring to a mixture of 11$\beta$-formylestr-4-ene-3,17-dione (I, Example 1', 25g) in methylene chloride (28 liters, deoxygenated by vacuum). The mixture is stirred at 20°–25° for 24 hours after which the mixture is cooled on an ice bath and ice is added to the reaction mixture very slowly. The organic phase is separated and washed several times with water and bicarbonate dried and concentrated to a solid.

The 11$\beta$-difluoromethyl (II) and the (E)-11-(fluoromethylene) products are separated by chromatography on silica gel. The column is eluted with a THF/hexane mixture (30/70). A 30 or 40% ethyl acetate and hexane mixture works equally well. The appropriate fractions are pooled, concentrated at a reduced pressure to give the title compound.

EXAMPLE 3

11$\beta$-Difluoromethylestr-4-ene-3,17-dione 3-ethanedithiol ketal (IV)

Ethanedithiol (0.27 ml) and boron trifluoride etherate 2 drops is added to a mixture of 11$\beta$-difluoromethylestr-4-ene-3,17-dione (II, Example 2, 0.4 g) in methanol (2 ml). The mixture is kept in a cold-water bath. After a few minutes scratching induced crystal formation. The mixture is cooled in an ice bath, crystals collected, washed and dried to give the title compound, NMR (CDCl$_3$) 0.90, 0.33, 5.65 and 5.97 $\delta$.

EXAMPLE 4

17$\alpha$-Ethynyl-11$\beta$-difluoromethyl-17$\beta$-hydroxyestr-4-ene-3-one 3-ethanedithiol ketal (V)

A mixture of solid potassium t-butoxide (0.112 g) and THF (2.3 ml) under a nitrogen atmosphere is cooled in an ice-salt bath and saturated with acetylene gas. 11$\beta$-Difluoromethylestr-4-ene-3,17-dione 3-ethanedithiol ketal (IV, Example 3, 0.21 g) and THF (2 ml) is added dropwise with cooling. After a few minutes TLC (alumina plates) developed with 1/1 ethyl acetate-hexane shows one spot moving just slower than the starting material. Water is added and the product is extracted with diethyl ether. The diethyl ether is evaporated to give the title compound, NMR (CDCl$_3$) 0.88, 3.32, 5.60 and 6.0 δ.

EXAMPLE 5

17α-Ethynyl-11β-difluoromethyl-17β-hydroxyestr-4-ene-3-one (VIII)

17α-Ethynyl-11β-difluoromethyl-17β-hydroxyestr-4-ene-3-one 3-ethanedithiol ketal (V, Example 4,) is dissolved in acetone (10 ml) methyl iodide (0.4 ml) in a few drops of water. The flask is stoppered and the mixture heated at 30°-35° for 4 days. A mixture of aqueous sodium bisulfite and diethyl ether are added and the mixture shaken vigorously to dispell the iodine color. The diethyl ether is separated, washed with bicarbonate and water, dried, concentrated to dryness and chromatographed through silica gel. The appropriate fractions are pooled, concentrated to a solid which is crystallized from acetone-SSB to give the title compound, NMR (CDCl$_3$) 0.93, 0.60, 5.85 and 6.08 δ; mp 185°-187°; UV (ethyl alcohol) $\lambda_{max}$=239 nm (ε=17,200); IR (mull) 3547, 3240, 2107, 1668, 1624 cm$^{-1}$; MS (m/e) 348, 330, 297 and 281.

EXAMPLE 6

11β-Difluoromethyl-17β-hydroxy-17α-propynylestr-4-en-3-one-3-ethanedithiol ketal (V)

Propynyl magnesium chloride (1 ml) in THF (about 1M) is added to a mixture of 11β-difluoromethylestr-4-ene-3,17-dione 3-ethanedithiol ketal (IV, Example 3, 0.2 g) and purified dry THF (5 ml) in dry equipment. The mixture is kept at 20°-25° for 18 hours at which time TLC (aluminum plates developed with 20/80:ethyl acetate/hexane) showed one spot moving just slower than the starting material. Diethylether and saturated aqueous ammonium chloride are added and the diethyl ether phase is separated, washed, dried and concentrated to give a solid foam of the title compound, NMR (CDCl$_3$) 0.86, 0.88, 0.83, 5.60 and 6.0 δ.

EXAMPLE 7

11β-Difluoromethyl-17β-hydroxy-17α-propynylestr-4-en-3-one (VIII)

11β-Difluoromethyl-17β-hydroxy-17α-propynylestr-4-en-3-one 3-ethanedithiol ketal (V, Example 6) is dissolved in acetone (15 ml) containing methyl iodide (0.6 ml) and water (0.5 ml) and heated at 40° for 3 days. Water, diethyl ether and diluted sodium bisulfite are added. The diethyl ether phase is separated, washed with bisulfite solution, saline, dried, concentrated under reduced pressure. The concentrate is chromatographed over a silica gel column using 1/1 ethyl acetate/hexane as the solvent system. Appropriate fractions are pooled, concentrated under reduced pressure to give a solid, then crystallized from acetone/hexane to give the title compound, mp 191°-193°; UV (ethyl alcohol) $\lambda_{max}$=238 nm (ε=16,850); IR (mull) 3483, 2200, 1659 and 1626 cm$^{-1}$; NMR (CDCl$_3$) 0.89, 1.63, 5.82 and 6.05 δ and MS (m/e) 362, 344, 334 and 281.

EXAMPLE 8

17α-Ethynyl-11β-difluoromethyl-17β-methoxyestr-4-en-3-one 3-ethanedithiol ketal (VI)

A dry flask under nitrogen pressure is charged with 0.6 g of sodium hydride (60% in mineral oil) and washed with hexane. The dry sodium hydride is slurried in dry THF (30 ml) and a mixture of 17α-ethynyl-11β-difluoromethyl-17β-hydroxyestr-4-en-3-one 3-ethanedithiol ketal (V, Example 4, 3 g) in dry THF (10 ml) is added with stirring. Methyl iodide (0.75 ml) is added and the mixture stirred overnight. TLC then shows the reaction to be complete. Saturated ammonium chloride is added slowly, the product is extracted with diethyl ether, the diethyl ether is washed, dried and concentrated to a thick oil which is the title compound.

EXAMPLE 9

17α-Ethynyl-11β-difluoromethyl-17β-hydroxyestr-4-en-3-one 17-methyl ether (VIII)

Following the general thiol ketal hydrolysis procedure of Examples 5, 7, 33 and 35 and making non-critical variations but starting with 17α-ethynyl-11β-difluoromethyl-17β-hydroxyestr-4-en-3-one 3-ethanedithiol ketal (VI, Example 8) and using acetone (225 ml), ethyl iodide (9 ml) and water (7.5 ml) the title compound is obtained, m.p. 181-184; NMR (CDCl$_3$) 0.90, 2.6, 3.38, 5.84 and 6.05 δ; UV (ethyl alcohol) $\lambda_{max}$=238 nm (ε=17400); IR (mull) 3069, 1727 and 1638 cm$^{-1}$; MS (m/e) 362, 347, 330 and 82.

EXAMPLE 10

17α-Ethynyl-11β-difluoromethyl-17β-hydroxyestr-4-ene-(VII)

A mixture of 17α-ethynyl-11β-difluoromethyl-17β-hydroxyestr-4-en-3-one 3-ethanedithiol ketal (V, Example 4, 2 g) and dry THF (10 ml) is added to a mixture of sodium (1 g) in liquid ammonia (40 ml) at −40°. The addition requires about 30 minutes, the reaction is quenched with solid ammonium chloride and then with ethanol. The ammonia is removed under reduced pressure, the product is extracted with methylene chloride, the methylene chloride extract is washed, dried and concentrated to a solid which is chromatographed on silica gel. The appropriate fractions are pooled, concentrated to a solid which is purified by crystallization to give the title compound.

EXAMPLE 11

17α-Ethynyl-11β-difluoromethyl-17β-hydroxyestr-4-ene (VII)

Following the general procedure of Example 10 and making non-critical variations but starting with 17α-ethynyl-11β-difluoromethyl-17β-hydroxyestr-4-en-3-one 3-ethanedithiol ketal 17-methyl ether (VI, Example 8) the title compound is obtained.

EXAMPLE 12

11β-Difluoromethylestr-4-en-3-one 3-ethanedithiol ketal 17-ethylene glycol ketal (IX)

p-TSA (25 mg) is added to a mixture of 11β-difluoromethylestr-4-ene-3,17-dione 3-ethanedithiol ketal (IV, Example 3, 3.5 g) in methylene chloride (20 ml), ethylene glycol (8 ml) and triethylorthoformate (6 ml). The mixture is kept for 20 hours at 20°-25° and then washed with bicarbonate solution and water. The organic phase is dried over magnesium sulfate and concentrated to an oil. The oil is triturated with SSB containing 1 drop of pyridine and a little methanol to give crystals of the title compound, NMR (CDCl$_3$) 0.88, 3.32, 3.86, 5.60 and 5.98 δ.

EXAMPLE 13

11β-Difluoromethylestr-4-en-3-one 17-ethylene glycol ketal (X) and 11β-difluoromethylestr-3-en-17-one 17-ethylene glycol ketal (XI)

A mixture of 11β-difluoromethylestr-4-en-3-one 3-ethanedithiol ketal 17-ethylene glycol ketal (IX, Example 12, 3.3 g) in THF (18 ml) is added to a mixture of lithium wire (0.37 g) and liquid ammonia (45 ml). The addition is done over a period of 5 minutes and after 15 more minutes the reaction mixture is quenched with solid ammonium chloride. Ethanol/hexane (1/5, 30 ml) is added and most of the ammonia boiled off. The organic phase is separated, washed several times with water, dried over magnesium sulfate, and concentrated to a colorless oil containing the mixture of the title compounds.

EXAMPLE 14

11β-Difluoromethylestr-4-en-17-one (XII) and 11β-difluoromethylestr-3-en-17-one (XIII)

The mixture of the 3-deoxy steroids from Example 13 is dissolved in acetone (12 ml) and hydrochloric acid (2N, 2.0 ml) is added. After 2 hours the product is extracted with diethyl ether which is washed and dried. The organic solvent is removed and the solid is chromatographed through a silver nitrate impregnated silica gel column using ethyl acetate/heptane (20/80) as the irrigant. The appropriate fractions are pooled, concentrated to give the title compound. The Δ-4 isomer has the following physical characteristics, NMR (CDCl$_3$) 0.91, 5.37 and 5.95 δ; IR (neat) 1740 cm$^{-1}$; MS (m/e) 308, 390, 380, 264, 251 and 94.

The Δ-3 isomer is obtained by pooling the appropriate fractions which are concentrated to give the title compound which has the following physical characteristics, NMR (CDCl$_3$) 0.90, 5.5 and 5.90 δ; IR (mull) 1720 cm$^{-1}$.

EXAMPLE 15

17α-Ethynyl-11β-difluoromethyl-17β-hydroxyestr-4-ene (VII)

Following the general procedure of Example 4 and making non-critical variations but starting with 11β-difluoromethylestr-4-en-17-one (XII, Example 14) the title compound is obtained; NMR (CDCl$_3$) 0.89, 2.59, 5.38 and 6.0 δ; IR (mull) 3437, 3305 and 1708 cm$^{-1}$; MS (m/e) 334, 316, 301, 279 and 266.

EXAMPLE 16

11β-Difluoromethyl-17β-hydroxy-17α-propynylestr-4-ene (VII)

A mixture of 11β-difluoromethylestr-4-en-17-one (XII, Example 14, 0.9 g) in propynyl magnesium bromide (0.5M, 10 ml) and THF is kept at 20°–25° for 16 hours. Diethyl ether and aqueous ammonium chloride are added and the diethyl ether phase is separated and washed with water and concentrated to a solid. The solid is purified by chromatography through silica gel using ethyl acetate/hexane (20/80) as the irrigant. The appropriate fractions are pooled and concentrated to give the title compound, IR (mull) 3400, 2237 and 1666 cm$^{-1}$; MS (m/e) 348, 330, 315, 266 and 251; NMR (CDCl$_3$) 0.87, 1.86 and 6.0 δ.

EXAMPLE 17

11β-Difluoromethyl-17β-hydroxy-17α-propynylestr-3-ene (VII)

Following the general procedure of Example 16 and making non-critical variations but starting with 11β-difluoromethylestr-3-en-17-one (XIII, Example 14, 0.14 g) the title compound is obtained which has the following physical characteristics, IR (mull) 3450, 2241 and 1650 cm$^{-1}$; MS (m/e) 348, 330, 320, 302, 264, 95, 82 and 67; NMR (CDCl$_3$) 0.86, 1.88, 5.51 and 5.95 δ.

EXAMPLE 18

17α-Ethynyl-11β-difluoromethyl-17β-hydroxyestr-4-ene 17-methyl ether (VII)

Following the general procedure of Example 8 and making non-critical variations but starting with 17α-ethynyl-17β-difluoromethyl-17β-hydroxyestr-4-ene (VII, Example 15) the title compound is obtained.

EXAMPLE 19

11β-Difluoromethylestr-5(10)-ene-3,17-dione 3-ethylene glycol ketal (XIV) and 11β-difluoromethylestr-5-ene 3,17-dione 3-ethylene glycol ketal (XV)

Following the general procedure of Example 12 but starting with 11β-difluoromethylestr-4-ene-3,17-dione (II, Example 2) and using only 25% of the p-TSA catalyst and the reaction conducted at 20°–25° for careful control to minimize the amount of bis-ketal. The Δ$^5$ and Δ$^{5(10)}$-dienes are produced and are separated by careful chromatography to give the title compound.

EXAMPLE 20

17α-Ethynyl-11β-difluoromethyl-17β-hydroxyestr-5(10)-en-3-one 3-ethylene glycol ketal (XVI)

Following the general procedure of Examples 4 and 6 and making non-critical variations but starting with 11β-difluoromethylestr-5(10)-ene, 3,17-dione-3-ethylene glycol ketal (XIV, Example 19) the title compound is obtained.

EXAMPLE 21

17α-Ethynyl-11β-difluoromethyl-17β-hydroxyestr-5(10)-en-3-one (XVII)

17α-Ethynyl-11β-difluoromethyl-11β-hydroxyestr-5(10)-en-3-one 3-ethylene glycol ketal (XVI, Example 20) is hydrolyzed without isomerization of the 5(10) double bond by the method of Conia et al., in Synthesis 63 (1978).

EXAMPLE 22

17α-Ethynyl-11β-difluoromethyl-17β-hydroxyestra-4,9-dien-3-one (XVIII)

17α-Ethynyl-11β-difluoromethyl-17β-hydroxyestr-5(10)-en-3-one (XVII, Example 21) is converted to the corresponding Δ$^{4,9}$-diene by bromination, dehydrobromination as described by Perelman et al., in J. Am. Chem. Soc., 82, 2402 (1960).

EXAMPLE 23

7α-Methylestr-4-ene-3,11,17-trione (B)

A mixture of 11α-hydroxy-7α-methylestr-4-ene-3,17-dione (A, obtained from Fermentation) and acetic acid (7.5 ml) is stirred and cooled to about 10° in a cold water bath. The following reagents are added: water (6 drops), manganese sulfate monohydrate (0.1 g) in water (1 ml), chromium trioxide (0.66 g) in water (2 ml), and concentrated sulfuric acid (0.6 ml). The chromium trioxide solution is added over a 15 minute period. After ½ hour water (10 ml) is added and the crystals of the product are collected, washed with water and dried to give a solid. The solid is dissolved in hot ethyl acetate/methylene chloride (1/1) and decolorized with a little charcoal and silica gel and then filtered through celite. The appropriate fractions are pooled and concentrated to give crystals, UV (ethyl alcohol) $\lambda_{max}$=239 nm ($\epsilon$=16250); IR (mull) 1740, 1707, 1672 and 1616; MS (m/e)=300, 282, 272, and 258.

EXAMPLE 24

7α-Methylestr-5-ene-3,11,17-trione 3,17-bis ketal (C)

A mixture of 7α-methylestr-4-ene-3,11,17-trione (B, Example 23, 4.1 g), methylene chloride (50 ml), ethylene glycol (31 ml), triethylorthoformate (14 ml) and p-TSA (41 mg) are refluxed for 3 hours. The mixture is then cooled and washed with bicarbonate and water, then dried to a solid. NMR shows a mixture of Δ5 (10) and Δ5 isomers. The product is used without further purification.

EXAMPLE 25

11-Methoxymethylene-7α-methylestr-5-ene-3,17-dione 3,17-bisethylene glycol ketal (D)

Following the general procedure of Preparations 3 and 3' and making non-critical variations but starting with 7α-methylestr-5-ene-3,11,17-trione 3,17-bis ketal (C, Example 24), about 5 g of the bis ketal is processed to give the title compound, NMR (CDCl$_3$) 0.78, 0.72, 3.55, 3.92, 3.93, 5.5 and 5.86 δ.

EXAMPLE 26

11β-Formyl-7α-methylestr-4-ene-3,17-dione (I)

11-Methoxymethylene-7α-methylestr-5-ene-3,17-dione 3,17-bisethylene ketal (D, Example 25) is dissolved in acetone (100 ml) and the mixture deoxigenated under reduced pressure and nitrogen. Hydrochloric acid (6N, 0.4 ml) is added. After 3 hours the mixture is neutralized with bicarbonate and the product is extracted with diethyl ether to give the title compound, NMR (CDCl$_3$) 0.82, 5.8 and 9.86 δ.

EXAMPLE 27

11β-Difluoromethyl-7α-methylestr-4-ene-3,17-dione (II) and
(E)-11-fluoromethylene-7α-methylestr-4-ene-3,17-dione (III)

A mixture of 11β-formyl-7α-methylestr-4-ene-3,17-dione (I, Example 26, 1.9 g) in methylene chloride (20 ml) and DAST (4 ml) is stirred under argon for 20 hours. The reaction mixture is poured into a mixture of diethyl ether and ice. The steroid product is extracted with diethyl ether and chromatographed through silica gel. The appropriate fractions are pooled and concentrated to give the title compounds, respectively.

EXAMPLE 28

11β-Difluoromethyl-7α-methylestr-4-ene-3,17-dione 3-ethanedithiol ketal (IV) and
(E)-11-fluoromethylene-7α-methylestr-4-ene-3,17-dione 3-ethanedithiol ketal (IV')

Following the general procedure of Examples 3 and 31 and making non-critical variations but starting with 11β-difluoromethyl-7α-methylestr-4-ene-3,17-dione (II, Example 27) and (E)-11-fluoromethylene-7α-methylestr-4-ene-3,17-dione (III, Example 27) the title compounds are obtained.

EXAMPLE 29

11β-Difluoromethyl-17β-hydroxy-7α-methyl-17α-propynylestr-4-en-3-one (VIII) and
(E)-11-fluoromethylene-17β-hydroxy-7α-methyl-17α-propnylestr-4-en-3-one (VIII')

Following the general procedures of Examples 4 and 5, 6 and 7, 32 and 33, 34 and 35, and making non-critical variations but starting with 11β-difluoromethyl-7α-methylestr-4-ene-3,17-dione 3-ethanedithiol ketal (IV, Example 28) and (E)-11-fluoromethylene-7α-methylestr-4-ene-3,17-dione 3-ethanedithiol ketal (IV', Example 28) a mixture of the title compounds are obtained. This mixture is dissolved in methylene chloride and adsorbed on silica gel (6 g). The solvent is evaporated in a rotary evaporator and the dried silica gel is packed in a precolumn and attached to 2 Merck Size B Prepacked columns (new and not equilibrated). A solvent mixture of ethyl acetate/hexane (30/70) is pumped through and 8 ml fractions are collected. Fractions 76–79 contained the fluoromethylene compound (VIII') and fractions 80 and 81 were mixtures and fractions 82–92 contained the difluoromethyl compound (VIII).

Fractions 76–79 are concentrated to a solid recrystallized from acetone-SSB to give the fluoromethylene compound (VIII'), UV (ethyl alcohol) $\lambda_{max}$=239 nm ($\epsilon$=16900); IR (mull) 3407, 1674, 1645 and 1622 cm$^{-1}$; MS (m/e) 356, 341, 314, 275, and 247; NMR (CDCl$_3$) 0.80, 0.84, 1.87, 5.87 and 6.60 δ.

Fractions 82–92 are combined, concentrated to a solid and recrystallized from acetone to give the difluoromethyl steroid (VIII), UV (ethyl alcohol) 239 nm ($\epsilon$=17300); IR (mull) 2924, 1662 and 1620 cm$^{-1}$; MS (m/e) 376, 358, 336, 318 and 295; NMR (CDCl$_3$) 0.79, 0.88, 1.87, 5.85 and 6.06 δ.

EXAMPLE 30

17α-Ethynyl-11β-difluoromethyl-17β-hydroxy-7α-methyl estr-4-en-3-one (VIII) and
17α-ethynyl-(E)-11-fluoro methylene-17β-hydroxy-7α-methylestr-4-en-3-one (VIII')

Following the general procedure of Examples 4 and 5, 6 and 7, 32 and 33, 34 and 35 and making non-critical variations but starting with a mixture of 11β-difluoromethyl-7α-methylestr-4-ene-3,17-dione 3-ethanedithiol ketal (IV, Example 28) and (E)-11-fluoromethylene-7α-methylestr-4-ene-3,17-dione 3-ethanedithiol ketal (IV', Example 28) a mixture of the title compounds is obtained. The mixture is separated by chromatography by the procedure of Example 29. The 11-fluoromethylene steroid (VIII') is crystallized from acetone-SSB to give the title compound, UV (ethyl alcohol) 239 nm ($\epsilon$=16600); IR (mull) 3365, 3251, 1678, 1654 and 1611 cm$^{-1}$; MS (m/e) 342, 324, 300, 275 and 259; NMR (CDCl$_3$) 0.81, 0.87, 2.61, 5.90 and 6.60 δ.

The fractions containing the 11β-difluoromethyl isomer (VIII) are combined, concentrated to a solid which is recrystallized from acetone-SSB to give the title compound (VIII), UV (ethyl alcohol) 239 nm (ε=17550); IR (mull) 3389, 3039, 1656 and 1611 cm$^{-1}$; MS (m/e) 362, 344, 329, 311 and 295; NMR (CDCl$_3$) 0.77, 0.91, 2.63, 5.85 and 6.05 δ.

EXAMPLE 31

(E)-11-(fluoromethylene)-estr-4-ene-3,17-dione 3-ethanedithiol ketal (IV')

Ethanedithiol (1.5 ml) and boron trifluoride etherate is added to a slurry of (E)-11-(fluoromethylene)-estr-4-ene-3,17-dione (III, Example 2, 2.0 g) and methanol (10 ml) under nitrogen. After stirring 1 hour the mixture is chilled and filtered. The solid is washed with a little cold methanol then with water. The solids are dried to give the title compound, NMR (CDCl$_3$) 0.87, 2.95, 3.10, 3.33, 5.67 and 6.55 δ; MS (m/e) 378, 350, 318 and 285; IR (mull) 1740, 1677, 1647 and 1076 cm$^{-1}$.

EXAMPLE 32

17α-Ethynyl-(E)-11-fluoromethylene-17β-hydroxyestr-4-en-3-one 3-ethanedithiol ketal (V')

Dry solid potassium t-butoxide (300 mg) and dry THF (6.1 ml) are degassed and cooled in an ice bath. Acetylene gas is bubbled in for 15 minutes and then a solution of (E)-11-(fluoromethylene)-estr-4-ene-3,17-dione 3-ethanedithiol ketal (IV', Example 31, 520 mg) and dry THF (5.3 ml) is added. After 15 minutes TLC shows reaction to be complete. Water is added and the product extracted with diethyl ether. The diethyl ether extract is concentrated and carried on to the next reaction without purification, NMR (CDCl$_3$) 0.84, 2.59, 3.32, 5.62 and 6.5 δ.

EXAMPLE 33

17α-Ethynyl-(E)-11-fluoromethylene-17β-hydroxyestr-4-en-3-one (VIII')

17α-Ethynyl-(E)-11-fluoromethylene-17β-hydroxyestr-4-en-3-one 3-ethanedithiol ketal (V', Example 32, 520 mg) are stirred at 40° for 3 days. The product is obtained by usual work-up procedures, chromatographed, recrystallized from acetone-SSB to give the title compound, mp 188°-190° C.; NMR (CDCl$_3$) 0.87, 2.60, 5.86 and 6.57 δ; UV (ethyl alcohol) λ$_{max}$=238 nm (ε=16,065), 305 nm (ε=138); IR (mull) 3428, 3274, 3251, 2102, 1680 and 1609 cm$^{-1}$; MS (m/e) 328, 313, 286 and 361.

EXAMPLE 34

(E)-11-fluoromethylene-17β-hydroxy-17α-propynylestr-4-en-3-one 3-ethanedithiol ketal (V')

Following the general procedure of Example 6 and making non-critical variations but starting with (E)-11-(fluoromethylene)-estr-4-ene-3,17-dione 3-ethanedithiol ketal (IV', Example 31, 1.5 g) the title compound is obtained which is purified by chromatography through alumina, NMR (CDCl$_3$) 0.82, 1.85, 3.3, 5.63 and 6.5 δ.

EXAMPLE 35

(E)-11-fluoromethylene-17β-hydroxy-17α-propynylestr-4-ene-3-one (VIII')

Following the general thiol ketal hydrolysis procedure of methyl iodide/water/acetone of Examples 7 and 33 the mixture is reacted at 45° for 3 days. The product is purified by chromatography through silica gel and recrystallized from acetone-SSB to give the title compound, UV (ethyl alcohol) λ$_{max}$=238 nm (ε=16350); IR (mull) 3457, 1675, 1654 and 1625 cm$^{-1}$; MS (m/e) 242, 327, 309 and 261; NMR (CDCl$_3$) 0.85, 1.87, 5.85 and 6.6 δ.

EXAMPLE 36

17α-Ethynyl-11β-difluoromethyl-17β-hydroxyestr-4-en-3-one 17-acetate 3-ethanedithiol ketal (VI)

A mixture of 17α-ethynyl-11β-difluoromethyl-17β-hydroxyestr-4-en-3-one 3-ethanedithiol ketal (V, Example 4, 500 mg), pyridine (0.5 ml) and acetic anhydride (0.5 ml) are kept at 20°-25° for 24 hours. TLC shows no reaction so 4-dimethylaminopyridine (100 mg) is added and the reaction mixture is kept at 20°-25° for 24 hours. TLC shows the reaction almost complete. The product is isolated by extraction and chromatographed to give the title compound.

EXAMPLE 37

17α-Ethynyl-11β-difluoromethyl-17β-hydroxyestr-4-en-3-one 17-acetate (VIII)

Following the usual thiol ketal hydrolysis procedure of Examples 5, 7, 33 and 35 and making non-critical variations and using acetone (16 ml), methyl iodide (0.65 ml), water (0.5 ml) and heating the reaction mixture in a sealed vessel at 40° for 4 days the title compound is obtained, mp 157°-180°; NMR (CDCl$_3$) 0.95, 2.05, 2.65, 5.85 and 6.06 δ.

EXAMPLE 38

11β-Difluoromethyl-17β-hydroxy-17α-propynylestr-4-en-3-one 17-acetate 3-ethanedithiol ketal (VI)

Following the general procedure of Example 36 and making non-critical variations but starting with 11β-difluoromethyl-17β-hydroxy-17α-propynylestr-4-en-3-one 3-ethanedithiol ketal (V, Example 6, 500 mg), pyridine (0.5 ml), acetic anhydride (0.5 ml), and 4-dimethylaminopyridine (100 ml) the title compound is obtained.

EXAMPLE 39

11β-Difluoromethyl-17β-hydroxy-17α-propynylestr-4-en-3-one 17-acetate (VIII)

Following the usual thiol ketal hydrolysis procedure of Examples 5, 7, 33 and 35 and making non-critical variations but starting with 11β-difluoromethyl-17β-hydroxy-17α-propynylestr-4-en-3-one 17-acetate 3-ethanedithiol ketal (V, Example 35, 50 mg) and using acetone (3.75 ml), methyl iodide (0.15 ml) and water (0.12 ml), the title compound is obtained, mp 175-178; NMR (CDCl$_3$) 0.90, 1.86, 2.02, 5.85 and 6.06 δ.

EXAMPLE 40

(E)-11-fluoromethylene-17β-hydroxy-17α-propynylestr-4-en-3-one 17-methyl ether 3-ethanedithiol ketal (VI′)

Sodium hydride (0.16 g of a 60% mineral oil suspension) is placed in a dry flask in an argon atmosphere. The sodium hydride is washed twice with hexane and dried with a stream of argon. (E)-11-fluoromethylene-17β-hydroxy-17α-propynylestr-4-en-3-one 3-ethanedithiol ketal (V′, Example 34, 0.3 g) in THF (5 ml) is added and after 10 minutes the mixture is cooled in an ice water bath and methyl iodide (0.4 ml) is added. After 1 hour water is added and the product extracted with diethyl ether to give the title compound, NMR (CDCl$_3$) 0.81, 1.92, 3.33, 3.38, 5.65 and 6.55 δ.

EXAMPLE 41

(E)-11-Fluoromethylene-17β-hydroxy-17α-propynylestr-4-en-3-one 17-methyl ether (VIII′)

Following the general thiol ketal hydrolysis procedure of Examples 5, 7, 33 and 35 and making non-critical variations but starting with (E)-11-fluoromethylene-17β-hydroxy-17α-propynylestr-4-en-3-one 17-methylether 3-ethanedithiol ketal (VI′, Example 40) and purifying the product by chromatography over silica gel followed by crystallization from acetone-SSB the title compound is obtained, UV (ethyl alcohol) λ$_{max}$=238 nm (ε=16700); IR (mull) 3110, 2224, 1674, 1665 and 1619 cm$^{-1}$; MS (m/e) 356, 341, 324, 309, 109 and 96; NMR (CDCl$_3$) 0.84, 1.91, 3.38, 5.86 and 6.55 δ.

EXAMPLE 42

11β-Difluoromethyl-17β-hydroxy-17α-propynylestr-4-en-3-one 17-methyl ether 3-ethanedithiol ketal (VI)

Following the general procedure of Example 40 and making non-critical variations but starting with 11β-difluoromethyl-17β-hydroxy-17α-propynylestr-4-en-3-one 3-ethanedithiol ketal (V, Example 6, 3 g) the title compound is obtained.

EXAMPLE 43

11β-Difluoromethyl-17β-hydroxy-17α-propynylestr-4-en-3-one 17-methyl ether (VIII)

Following the general thiol ketal hydrolysis procedure of Examples 5, 7, 33 and 35 and making non-critical variations but starting with 11β-difluoromethyl-17β-hydroxy-17α-propynylestr-4-en-3-one 17-methyl ether 3-ethanedithiol ketal (VI, Example 42) the title compound is obtained, mp 165°-167; NMR (CDCl$_3$) 0.92, 1.93, 3.39, 5.9 and 6.13 δ; UV (ethyl alcohol) λ$_{max}$=238 nm (ε=17200); IR (mull) 2242, 1669 and 1616 cm$^{-1}$; MS (m/e) 376, 361, 344, 109 and 96.

EXAMPLE 44

17α-Ethynyl-(E)-11-fluoromethylene-17β-hydroxyestr-4-ene (VII′)

Following the general procedure of Example 10 and making non-critical variations but starting with 17α-ethynyl-(E)-11-fluoromethylene-17β-hydroxyestr-4-en-3-one 3-ethanedithiol ketal (V′, Example 32) the title compound is obtained.

EXAMPLE 45

11β-Difluoromethyl-17β-hydroxyestr-4-en-3-one 17-methyl ether (VIII)

Sodium borohydride (0.1 g) is added to a mixture of 11β-difluoromethyl-estr-4-ene-3,17-dione 3-ethanedithiol ketal (IV, Example 3, 0.5 g) in ethanol (10 ml), water (1 drop), THF (2 ml) and methylene chloride (2 ml). After a few minutes, water is added and the mixture is concentrated to a few ml. The mixture is extracted with methylene chloride/diethyl ether. The extract is washed, dried and concentrated to a foam containing 11β-difluoromethyl-17β-hydroxyestr-4-en-3-one 3-ethanedithiol ketal (IV).

The 17β-hydroxy steroid is dissolved in dry/pure THF (5 ml) and sodium hydride (60% suspension, 0.1 g) and methyl iodide (0.12 ml) are added. The mixture is stirred overnight and the 17-methyl ether 3-ethanedithiol ketal intermediate is isolated by extraction.

The 3-ethanedithiol ketal protecting group is removed by dissolving the steroid in acetone (25 ml), water (1.5 ml) and methyl iodide (1 ml) and heated in a sealed flask at 40° for 3 days. The product is extracted and chromatographed thru silica gel eluting with ethyl acetate/hexane (30/70). The appropriate fractions are pooled and concentrated to a solid which is recrystallized from acetone-SSB, mp 119°-120°; NMR (CDCl$_3$) 0.82, 3.2, 3.33, 5.80 and 6.02 δ; MS (m/e) 338, 318, 306, 296 and 71; UV (ethyl alcohol) λ$_{max}$=239 nm (ε=17,000); IR (mull) 1672 and 1614 cm$^{-1}$.

EXAMPLE 46

11β-Difluoromethyl-17β-hydroxyestr-4-en-3-one (VIII)

A sodium borohydride solution (100 mg in 50 ml absolute ethanol, 4 ml) is added to a solution of 11β-difluoromethyl-estr-4-ene-3,17-dione (II, Example 2, 20 mg) in THF (4 ml) with cooling. After 1 hr another 1 ml of the borohydride solution is added. After 15 minutes acetic acid in water (5%, 10 ml) is added. Most of the solvent is removed under reduced pressure and the product extracted with diethyl ether. The product is chromatographed thru silica gel eluting with ethyl acetate/hexane (60/40). The appropriate fractions are pooled and concentrated to give the title compound, NMR (CDCl$_3$) 0.81, 3.63, 5.84, 6.05 and 55.5 δ.

EXAMPLE 47

(E)-11-(Fluoromethylene)estr-4-ene-3,17-dione (III) and (Z)-11-(Fluoromethylene)estr-4-ene-3,17-dione (Z)

A solution of 11β-formylestr-4-ene-3,17-dione (I, Example 1, 59 g) in acetonitrile (1180 ml) and water (3.54 ml) is deoxygenated under reduced pressure and covered with nitrogen. DAST (118 ml) is added with stirring. After 24 hr at 20°-25° the mixture is cooled in an ice bath and ice water is added slowly to avoid a violent reaction of the excess DAST with water. The product is extracted with diethyl ether, the extract washed with water and bicarbonate, concentrated, the concentrate chromatographed thru silica gel (100 g), two more columns are dry packed and connected in series. Elution was done by gradient between THF/hexane (20%-5 l and 30%-5 l) followed by THF/hexane (30%, 10 l). The Z isomer comes off the column first, then the E isomer, then the 11β-difluoromethyl compound. Fractions containing the E-isomers are pooled and triturated with cold methanol to give the (E)-11-fluoromethylene isomer; mp 118°–220.1°; NMR (CDCl$_3$) 0.92, 3.07, 5.88 and 6.63 δ; MS (m/e) 302, 282, 260, and 245; IR (mull) 1736, 1664 and 1610 cm$^{-1}$; UV (ethyl alcohol) λ$_{max}$=239 nm (ε=16,550) Fractions containing the Z-isomer are combined, concentrated under reduced pressure and crystallized from acetone/SSB to give the (Z)-11-fluoromethylene isomer; mp 151.9–153.1; NMR (CDCl$_3$) 0.89, 5.82 and 6.38 δ; MS (m/e) 302, 282 and 260; UV (ethyl alcohol) λ$_{max}$=239 (ε=16,350); IR (mull) 1742, 1673 and 1617 cm$^{-1}$.

EXAMPLE 48

(Z)-11-Fluoromethylene-17β-hydroxy-17-propynylestr-4-en-3-one (VIII″)

Pyrrolidine (0.15 ml) is added to (Z)-11-(fluoromethylene)estr-4-ene-3,17-dione (Z), Example 47, 0.13 g) in boiling methanol (1 ml). The enamine precipitates immediately. The mixture is chilled and the precipitated enamine is filtered and washed with a little cold methanol and dried under reduced pressure for 1 hour. To the enamine in a flask filled with nitrogen is added propynylmagnesium bromide (about 0.5M in THF/ether, 150/35, 2 ml). About one half hour is required for all of the enamine to dissolve. The solution is stirred for a total of 1.5 hours and the solution is diluted with ether and nearly saturated aqueous ammonium chloride. The ether layer is washed several times with water then concentrated to dryness to give the propynyl enamine intermediate, NMR (CDCl$_3$) 0.80, 1.86, 3.13, 4,84, 5.05 and 6.30 δ.

The crude propynyl enamine is dissolved in a deoxygenated mixture of acetic acid (1 ml) and water (2 ml) and heated at 65° for 3 hours. Most of the solvent evaporates on the rotary evaporator, then the concentrate is made slightly basic with sodium hydroxide (2N) and ether is added. The mixture is acidified with dropwise additions of hydrochloric acid (2N) then made basic again.

This is repeated 3 times to hydrolyze any remaining enamine. The ether layer is separated, washed and concentrated to a foam. It is chromatographed through a size B prepacked Merck silica column using ethyl acetate/hexane (40/60) as the irrigant. The product is recrystallized from ether-SSB to give the title compound; mp 147.5–148.5°; UV (ethyl alcohol) λ$_{max}$=239 nm (ε=16,500); MS (m/e) 342, 327, 309 and 361; IR (mull) 3472, 1674, 1656, 1625 cm$^{-1}$; NMR (CDCl$_3$) 0.84, 1.87, 5.84 and 6.3 δ.

EXAMPLE 49

17α-Ethynyl-(Z)-11-fluoromethylene-17β-hydroxyestr-4-en-3-one (VIII″)

Boron trifluoride etherate (3 drops) and ethanedithiol (0.4 ml) are added to a slurry of (Z)-11-(fluoromethylene)estr-4-ene-3,17-dione (Z, Example 47, 0.5 g) in methanol (2 ml), chilled in an ice bath. The mixture soon became clear and on scratching the thioketal precipitates. The mixture is kept at 20°–25° for 1 hour, chilled and filtered. The precipitate is washed with cold methanol, water and dried, give the 17-keto thioketal, NMR (CDCl$_3$) 0.86, 3.33 and 6.3 δ.

The thioketal (272 mg) is ethynylated with acetylene-potassium t-butoxide in THF as described in Example 4 to give the ethynylated thioketal; NMR (CDCl$_3$) 0.83, 2.60, 3.33, 5.61 and 6.25 δ.

The thioketal protecting group is removed by heating at 40° for 3 days in a mixture of acetone (20 ml), methyl iodide (0.81 ml) and water (0.68 ml).

The product was purified by chromatography through silica gel eluting with ethyl acetate/hexane (30/70) and recrystallizing from acetone-SSB, to give the title compound; mp 228–230; IR (mull) 339, 2100, 1676, 1652, 1625 and 1615 cm$^{-1}$; MS (m/e) 328, 313, 286 and 261; NMR (CDCl$_3$) 0.86, 2.60, 5.84, 6.3 δ.

EXAMPLE 50

(E)-11-Fluoromethylene-17β-hydroxy-17α-methylestr-4-en-3-one (VIII′)

To toluene (10 ml) in a dried flask under a nitrogen atmosphere is added lithium perchlorate (94 mg) and methylmagnesium bromide (3M in ether, 1.85 ml) with stirring and cooling in a cold water bath. After 10 minutes (E)-11-(fluoromethylene)estr-4-en-3,17-dione 3-enthanedithiol ketal (IV′, Example 31, 1 g) is added and after 1½ hours reaction time, solid sodium sulfate is added and the toluene phase was decanted and concentrated to dryness to give the 17α-methylthioketal intermediate; NMR (CDCl$_3$) 0.90, 1.26, 3.32, 5.62 and 6.5 δ.

The thioketal is hydrolyzed by the usual methyl iodide acetone-water procedure at 45° for 3 days and the product is purified by chromatography through silica gel and recrystallized from acetone-SSB to give the title compound; mp 127°–131°; UV (ethyl alcohol) λ$_{max}$=239 nm (ε=15,700); IR (mull) 3373, 1672, and 1615 cm$^{-1}$; MS (m/e) 318, 298, 280, 260 and 240; NMR (CDCl$_3$) 0.89, 1.28, 5.88, 6.55 δ.

EXAMPLE 51

(E)-11-Fluoromethylene-17β-hydroxyestr-4-en-3-one (VIII′) and
(E)-11-fluoromethylene-17β-hydroxyestr-4-en-3-one 17-acetate (VIII′)

A mixture of (E)-11-(fluoromethylene)estr-4-ene-3,17-dione 3-ethanedithiol ketal (IV′, Example 31, 915 mg), 95% alcohol (19 ml), methylene chloride (7 ml), and sodium borohydride (100 mg) are kept at 20°–25° for 3 hr. Water is added and the product is extracted with methylene chloride and crystallized from acetone-SSB to give the 17β-hydroxy intermediate; NMR (CDCl$_3$) 0.74, 3.32, 3.75, 5.65 and 6.5 δ.

A mixture of this 17β-hydroxy intermediate (915 mg) in pyridine (0.95 ml) and acetic anhydride (0.48 ml) are kept at 20°–25° overnight. The mixture is diluted with water and extracted with ether to give C$_3$ protected 17-acetoxy (E)-11-fluoromethylene intermediate; NMR (CDCl$_3$) 0.78, 2.05, 3.32, 4.6, 5.66 and 6.47.

A mixture of the 17-acetoxy thioketal intermediate (0.95 g), acetone (7 ml), water (2.4 ml) and methyl iodide (2.85 ml) are heated in a sealed flask at 40° for 4 days. The products are obtained by extraction and separated by chromatography over silica gel. The appropriate fractions are pooled, concentrated to give solids. The 17β-hydroxy compound is recrystallized from acetone to give the title compound; mp 167–168.9; MS (m/e) 304, 284, 262, and 242; UV (ethyl alcohol) λ$_{max}$=239.5 nm (ε=15,700); IR (mull) 3264, 3197, 1673, 1616 cm$^{-1}$; NMR (CDCl$_3$) 0.77, 3.78, 3.88, 6.55 δ.

The 17-acetate title compound is recrystallized from acetone-SSB to give the title compound; mp 132–132.4; MS (m/e) 346, 326, 304 and 286; IR (mull) 3111, 1736, 1676, 1666, 1622 cm$^{-1}$; UV (ethyl alcohol) λ$_{max}$=239 nm (ε=16,756); NMR (CDCl$_3$) 0.81, 2.07, 4.71, 5.88 and 6.55 δ.

EXAMPLE 52

(E)-11-(Fluoromethylene)estrone (XIX-E)

(E)-11-(Fluoromethylene)estr-4-ene-3,17-dione (III, Example 2, 0.1 g), t-butyl alcohol (5 ml), and selenium dioxide (0.13 g) is refluxed under an argon atmosphere for 1.5 hr. The solvent is blown off by a stream of argon and the residue is stirred with methylene chloride (5 ml) and filtered through a bed of celite. The filtrate is chromatographed over silica gel and eluted with ethyl acetate/hexane (30/70). The appropriate fractions are pooled and concentrated to a solid which is crystallized from acetone-SSB to give the title compound; IR (mull) 3293, 1724, 1681 cm$^{-1}$;MS (m/e) 300, 285, 272 and 256; NMR (CDCl$_3$/CH$_3$OH) (CDCl$_3$ at 7.25 is the reference line) 0.78, 6.4, 7.0, and 6.95 δ.

The yield is doubled if the reaction is run at 60° for 3 hr and the chromatographic column is eluted with ethyl acetate/toluene (20/80).

EXAMPLE 53

(E)-11-(Fluoromethylene)estradiol (XX-E)

A mixture of (E)-11-(Fluoromethylene)estrone (XIX-E, Example 52, about 25 ml) and THF (5 ml) (heating is necessary to completely dissolve) is diluted with 95% ethyl alcohol (5 ml) and sodium borohydride (30 ml) is added. After 1 hr TLC developed with ethyl acetate/toluene (80/20) shows one spot moving slower than the starting material. The solvents are evaporated on a rotary evaporator and the residue triturated with water and the mixture filtered. The precipitate is dissolved in ethyl acetate/toluene (20/80) and a little THF and chromatographed using the same solvent mixture. The appropriate fractions are pooled and concentrated to give a residue which is crystallized from acetone-SSB to give the title compound; UV (ethyl alcohol) λ$_{max}$=281 nm (ε=1,700); IR (mull) 3593, 3280, 1679, 1622, 1584 cm$^{-1}$; MS (m/e) 302, 274, and 243; NMR (CDCl$_3$-CD$_3$OD) 3.80, 6.55, 6.5 and 7.15 δ.

EXAMPLE 54

(E)-11-Fluoromethylene-3β,17β-dihydroxy-17α-propynyl estr-5-ene (XXII)

A mixture of (E)-11-fluoromethylene-17β-hydroxy-17α-propynylestr-4-en-3-one (VIII', Example 35, 0.135 g and p-TSA 0.01 g) and acetic anhydride (1 ml) and toluene (3 ml) is refluxed under nitrogen atmosphere for 5.5 hr. The mixture is cooled and washed with water containing a little pyridine and followed by bicarbonate and water and dried over magnesium sulfate and concentrated to an oil. The oil is triturated with a little methanol to give the crystalline enol acetate (XXI); NMR (CDCl$_3$) 0.83, 2.08, 2.14, 5.5, 5.78 and 7.00 δ.

The enol acetate (XXI) is stirred with sodium borohydride (0.08 g) in 95% ethyl alcohol (2 ml) and degassed by vacuum, releasing the vacuum with nitrogen. The mixture is stirred for about 75 hr and the product is extracted with ethyl acetate/methylene chloride (1/1), washed well with water, concentrated to a crystalline solid which is chromatographed through silica gel. The appropriate fractions are pooled and concentrated to give a crystalline residue which is dried at 60° under reduced pressure to give the title compound; NMR (CDCl$_3$) 0.79, 1.87, 2.85, 3.5, 5.5 and 7.1 δ.

EXAMPLE 55

(E)-11-(Fluoromethylene)estr-4-en-17-one (XII')

Ethylene glycol (7.83 ml), triethyl orthoformate (5.78 ml) and pTSA (23.8 ml) are added to a mixture of (E)-11-(fluoromethylene)estr-4-ene-3,17-dione 3-ethanedithiol ketal (IV', Example 31, 3.4 g) and methylene chloride (19.38 ml). The mixture is allowed to stand at 20°-25° overnight. TLC shows the reaction to be complete. The 17-ketal product is extracted with methylene chloride and washed with dilute sodium bicarbonate and water and dried over sodium sulfate. The organic phase is filtered, the filtrate concentrated to give the 3-ethanedithiol ketal 17-ethylene glycol ketal (IX'); NMR (CDCl$_3$) 0.83, 3.32, 3.90, 5.65 and 6.47 δ.

Lithium wire (374 mg) is dissolved in liquid ammonia (43 ml). The 3,17-diprotected steroid (XI) is dissolved in THF (12.92 ml) and added dropwise over 1 hr to the lithium mixture. After stirring at reflux solid ammonium chloride is added and ammonia evaporated. A couple of drops of 95% alcohol are added and the product extracted with ether. The ether is washed several times with water, dried over sodium sulfate, filtered and concentrated to a solid residue which is the 3-deoxy 17-ethylene glycol ketal (X'). The material also contains the 11-methylene as an impurity. The mixture is hydrolized in acetone (12.2 ml) and hydrochloric acid (2N, 2 ml) at 20°-25° for 16 hr. The reaction mixture is distributed between water and ether and the layers are separated and the ether layer is washed with bicarbonate and water and dried and concentrated to a solid. The solid is chromatographed thru 2 silica gel columns eluting with ethyl acetate/hexane (5/95). The appropriate fractions are pooled and concentrated to give residue which is crystallized from acetone-SSB to give the title compound; mp 101–101.5; NMR (CDCl$_3$) 0.87, 5.5, 6.57 δ; IR (mull) 3102, 1744, 1679 cm$^{-1}$; MS (m/e) 288, 273, 260, 245 and 231.

EXAMPLE 56

(E)-11-Fluoromethylene-17β-hydroxy-17α-propynylestr-4-ene (VII')

(E)-11-(Fluoromethylene)estr-4-en-17-one (XII, Example 55, 382 ml) is cooled on an ice bath. Propynyl magnesium bromide (about 0.5M, 4.24 ml is THF) is added and the mixture stirred. After 2 hr TLC shows a small amount of starting material and an additional Grignard reagent is added (0.5 ml). After another 0.5 hr ice and water are added and the product extracted with ether, washed several times with water, dried over sodium sulfate, filtered, and concentrated. The residue is chromatographed over a silica gel column using ethyl acetate/hexane (10/90) as the irrigant. Fractions 39 to 45 are pooled and concentrated to give a solid which is crystallized from methanol/water to give the title compound; NMR (CDCl$_3$) 0.83, 1.86, 5.47, 6.53 δ; MS (m/e) 328, 313, 295 and 246; IR (mull) 3428, 1677 cm$^{-1}$.

EXAMPLE 57

17α-Ethynyl-17β-hydroxy-(E)-11-(fluoromethylene)estr-4-ene (VII')

Solid potassium t-butoxide (220.5 ml) and dry THF(4.5 ml) are mixed and cooled in ice bath. Acetylene gas is purged through the potassium tertiary butoxide solution for 15 minutes. A mixture of E-11-(fluoromethylene)estr-4-en-17-one (XII, Examples 55, 382 ml) and dry THF (3.9 ml) is added to the mixture, stirred and purged for another 15 minutes. After 15 minutes, TLC shows one spot. Water is added and the product extracted with ether. The ether extract is washed several times with water, dried over sodium sulfate, filtered and concentrated to a residue. The residue is chromatographed over a silica gel column using ethyl acetate/hexane (15/85) as the irrigant. The appropriate fractions are pooled and concentrated to a solid which is recrystallized from SSB at 5° to give the title compound; mp 103°-103.9°; NMR (CDCl$_3$) 0.85, 2.5, 5.4, 6.48 δ; MS (m/e) 314, 296, 281 and 246; IR (mull) 3603 cm$^{-1}$.

EXAMPLE 58

(E)-11-fluoromethylene-17β-hydroxy-17α-propynylestr-4-en-3-one (VIII′)

To a mixture of (E)-11-(fluoromethylene)estr-4-ene-3,17-dione (III, Example 2, 2.0 g) and boiling methanol (15 ml) is added pyrrolidine (2 ml). The boiling is continued until the dione starting material is dissolved and the enamiane precipitated. The mixture is chilled and filtered and the crystals of the enamine are washed with cold methanol and dried at 20°-25° under reduced pressure for 18 hours.

Pyrrolidine enamine is deoxygenated under reduced pressure and covered with nitrogen, then the propynyl magnesium bromide (about 0.5 M in THF) is added. After 1.5 hours at 20°-25° water (deoxygenated, 8 ml), methanol (24 ml), and sodium hydroxide (2N, 1 ml) are added. The mixture is refluxed for 1 hours and cooled to 20°-25°. The precipitate is collected and washed with water. The mother liquor and washings are combined and extracted with ether/methylene chloride to give additional product. The solids are combined and dissolved in boiling methylene chloride/acetone and filtered through a bed of celite and then through a short bed of silica gel. The beds are washed with acetone/methylene chloride (40/60) and filtrate washings are combined and boiled down with the addition of ethyl acetate. When the volume reaches about 25 ml, the solvent is essentially all ethyl acetate, crystals form. The mixture is chilled and filtered to give the title compound.

EXAMPLE 59

13β-Ethylgon-5-ene-3,11,17-trione 3,17-bisethylene glycol ketal (C-Et)

Following the general procedure of Preparation 2 and making non-critical variations but starting with 13β-ethylgon-4-ene-3,11,17-trione (B-Et, U.S. Pat. No. 4,031,074) the title compound is obtained.

EXAMPLE 60

13β-Ethyl-11β-formylgon-4-ene-3,17-dione (I-Et)

Following the general procedure of Example 1 and making non-critical variations but starting with 13β-ethylgon-5-ene-3,11,17-trione, 3,17-bisethylene glycol ketal (C-Et, Example 59) the title compound is obtained.

EXAMPLE 61

13β-Ethyl-11β-difluoromethylgon-4-ene-3,17-dione (II-Et),
13β-ethyl-(E)-11-fluoromethylenegon-4-ene-3,17-dione (III-Et) and
13β-ethyl-(Z)-11-fluoromethylenegon-4-ene-3,17-dione (Z-Et)

Following the general procedure of Example 47 and making non-critical variations but starting with 13-ethyl-11β-formylgon-4-ene-3,17-dione (I-Et, Example 60, 990 mg) the aldehyde (I-Et) is reacted with DAST in acetonitrile to give a mixture of products. The crude product (782 mg) is chromatographed over silica gel. The column is eluted with ethyl acetate/hexane (60/40).

Fractions 26-31 are pooled and concentrated to give 13β-ethyl-(Z)-11-fluoromethylenegon-4-ene-3,17-dione (Z-Et), NMR (CDCl$_3$) 0.75, 5.80 and 6.30 δ.

Fractions 33-38 are pooled and concentrated to give crystalline 13β-(E)-11-fluoromethylenegon-4-ene-3,17-dione (III-Et), mp 167.5°-172°; NMR (CDCl$_3$) 0.83, 5.90 and 6.56 δ; UV (95% ethanol) λ$_{max}$=239 nm (ε=16,400); IR (KBr) 3184, 1730, 1671, 1662 and 1614 cm$^{-1}$; MS (m/e) 316, 287, 274 and 245.

Fractions 41-51 are pooled and concentrated to give 13β-ethyl-11β-difluoromethylgon-4-ene-3,17-dione (II-Et), NMR (CDCl$_3$) 0.84 4.86 and 5.02 δ.

EXAMPLE 62

13β-Ethyl-(Z)-11-fluoromethylene-17β-hydroxy-17α-propynylgon-4-en-3-one (VIII-Et)

Pyrrolidine (1 drop) is added to 13β-ethyl-(Z)-11-fluoromethylenegon-4-ene-3,17-dione (Z-Et, Example 61, 10 mg) in warm methanol (10 drops) under nitrogen. After warming on the steam bath for about 1 min the enamine precipitates. The mixture is chilled, crystals form which are separated and washed with methanol and SSB (5 drops). The enamine intermediate is dried under reduced pressure and reacted with propynylmagnesium bromide (0.5M in THF, 0.35 ml). After 1 hr at 20°-25°, water (0.3 ml) methanol (0.9 ml) and sodium hydroxide (2N, 2 drops) are added and the mixture heated at 50° for 1 hr to hydrolyze the enamine. The mixture is cooled and made acidic with hydrochloric acid (6N) and stirred 1 hr. Water is added and the product is extracted with ether, and the organic phase is washed with a bicarbonate solution and water, concentrated and chromatographed thru silica gel eluting with ethyl acetate/hexane (40/60). The appropriate fractions are pooled and concentrated and the product is crystallized from hexane, mp 199°-205°; NMR (CDCl$_3$) 1.03, 1.86, 1.84 and 6.4 δ; MS (m/e) 356, 327, 309.

EXAMPLE 63

13β-Ethyl-17α-ethynyl-(E)-11-fluoromethylene-17β-hydroxygon-4-en-3-one (VIII-Et)

13β-Ethyl-(E)-11-fluoromethylenegon-4-ene-3,17-dione (III-Et, Example 61, 75 mg) is converted to the corresponding pyrrolidine enamine following the general procedure of Example 62 and making non-critical variations.

The enamine is dissolved in THF (0.9 ml) and added to a solution of potassium t-butoxide (43 mg) saturated with acetylene with cooling in an ice bath. After 15 min the 17α-ethynyl enamine is hydrolyzed following the general procedure of Example 62 and making non-critical variations. The product is chromatographed thru a silica gel column. The appropriate fractions are pooled and concentrated to give crystalline title compound, mp 169°–180°; MS (m/e) 342, 324, 314, 295 and 275; NMR (CDCl$_3$) 1.15, 2.62, 5.87 and 6.52 δ.

EXAMPLE 64

13β-Ethyl-(E)-11-fluoromethylene-17β-hydroxyl-17α-propynylgon-4-en-3-one (VIII-Et)

Following the general procedure of Example 62 and making non-critical variations but starting with 13β-ethyl-(E)-11-fluoromethylenegon-4-ene-3,17-dione (III-Et, Example 61, 12) the title compound is obtained, NMR (CDCl$_3$) 1.12, 2.7, 5.87 and 6.55 δ.

EXAMPLE 65

13β-Ethyl-11β-difluoromethyl-17β-hydroxy-17α-propynylgon-4-en-3-one (VIII-Et)

Following the general procedure of Example 62 and making non-critical variations but starting with 13β-ethyl-11β-difluoromethylgon-4-ene-3,17-dione the title compound is obtained, UV (alcohol) $\lambda_{max}$=239 nm (ε=16,750); IR (mull) 3422, 1664, 1619 cm$^{-1}$; MS (m/e) 276, 358, 347 and 295; NMR (CDCl$_3$) 1.15, 1.86, 5.84 and 6.03 δ.

TABLE 1

| Compound | Relative Binding Affinity' (%) | DAO Assay B.P. (Dose in mg) |
|---|---|---|
| 11β-Difluoromethyl-17β-hydroxyestr-4-en-3-one | 13 | |
| 17α-Ethynyl-11β-difluoromethyl-17β-hydroxyestr-4-ene-3-one 3-ethanedithiol ketal | 92 | 6 (.1) |
| 11β-Difluoromethyl-17β-hydroxy-17α-propynylestr-4-en-3-one | 68 | 8 (.1) |
| (E)-11-fluoromethylene-17β-hydroxy-17α-propynylestr-4-ene-3-one | 18 | 8 (.006) |
| 11β-Difluoromethyl-17β-hydroxy-17α-propynylestr-4-ene | 3 | 8 (.2*) |
| 11β-Difluoromethyl-17β-hydroxy-17α-propynylestr-3-ene | 2 | |
| 17α-Ethynyl-11β-difluoromethyl-17β-hydroxyestr-4-ene | 2 | 0 (.2*) |
| 11β-Difluoromethyl-17β-hydroxyestr-4-en-3-one 17-methyl | 66 | |
| 17α-Ethynyl-11β-difluoromethyl-17β-hydroxyestr-4-en-3-one 17-methyl ether | 145 | 69 (.05*) |
| 11β-Difluoromethyl-17β-hydroxy-17α-propynylestr-4-en-3-one 17-methyl ether | 90 | 206 (.05*) |
| 17α-Ethynyl-11β-difluoromethyl-17β-hydroxyestr-4-en-3-one 17-acetate | 50 | 129 (.05) |
| 11β-Difluoromethyl-17β-hydroxy-17α-propynylestr-4-en-3-one 17-acetate | 49 | 14 (.05) |
| 17α-Ethynyl-(E)-11-fluoromethylene-17β-hydroxyestr-4-en-3-one | 74 | 0 (.0125) |
| (E)-11-Fluoromethylene-17β-hydroxy-17α-propynylestr-4-en-3-one 17-methyl ether | 71 | 54 (.2) |
| (E)-11-Fluoromethylene-17β-hydroxy-7α-methyl-17α-propynylestr-4-en-3-one | 58 | 0 (.0125) |
| 11β-Difluoromethyl-17β-hydroxy-7α-methyl-17α-propynylestr-4-en-3-one | 41 | 0 (.05*) |
| 17α-Ethynyl-(E)-11-fluoromethylene-17β-hydroxy-7α-methylestr-4-en-3-one | 34 | 0 (.125) |
| 17α-Ethynyl-11β-difluoromethyl-17β-hydroxy-7α-methylestr-4-en-3-one | 63 | 0 (.05*) |
| 13β-Ethyl-(E)-11-fluoromethylene-17β-hydroxy-17α-propynylgon-4-en-3-one | 63 | >100 (.07) |
| (Z)-11-Fluoromethylene-17β-hydroxy-17-propynylestr-4-en-3-one | 150 | 100 (.01) |
| 17α-Ethynyl-(Z)-11-fluoromethylene-17β-hydroxyestr-4-en-3-one | 149 | 100 (.01) |
| 13β-Ethyl-(Z)-11-fluoromethylene-17β-hydroxy-17α-propynylgon-4-en-3-one | 149 | |
| 13β-Ethyl-17α-ethynyl-(E)-11-fluoromethylene-17β-hydroxygon-4-en-3-one | 100 | |

*Minimum dose to give near complete inhibition of DAO not yet determined.

In the DAO (diamine oxidase) assay when the BP (biopotency) value is 0, the test compound completely inhibits the progesterone induced DAO. When the value is 100 the test compound does not give any inhibition of the progesterone induced DAO enzyme. The lower the value the greater the antiprogestin activity of the test compound.

'Rabbit, progesterone=100%

CHART A

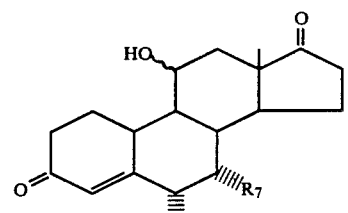

(A)

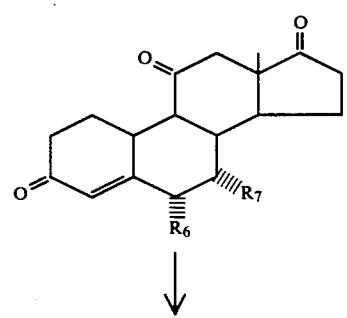

(B)

-continued
CHART A
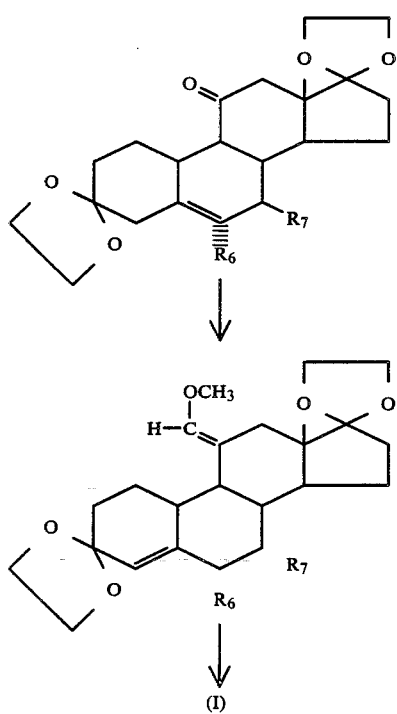
CHART B
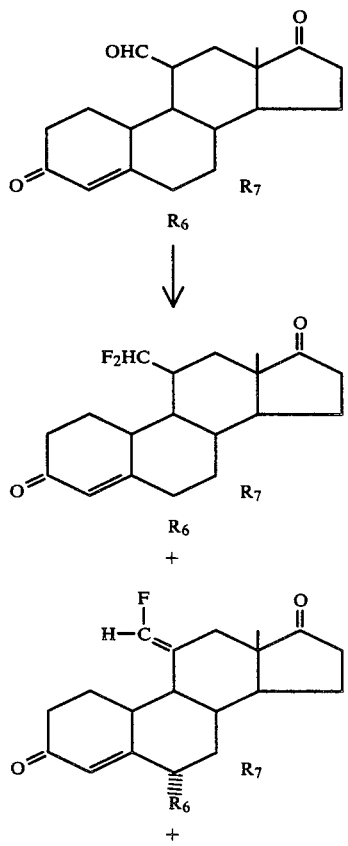
-continued
CHART B
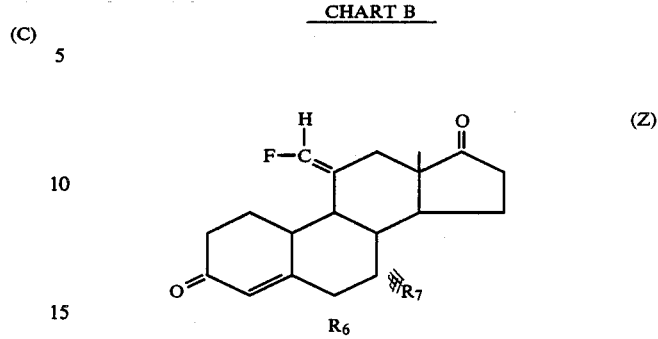
CHART C
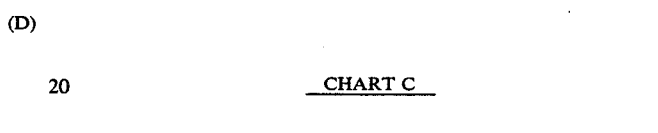
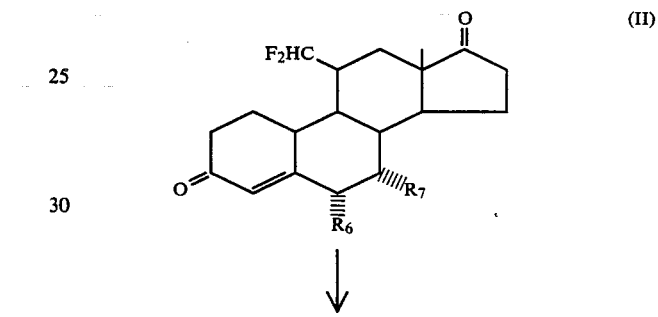
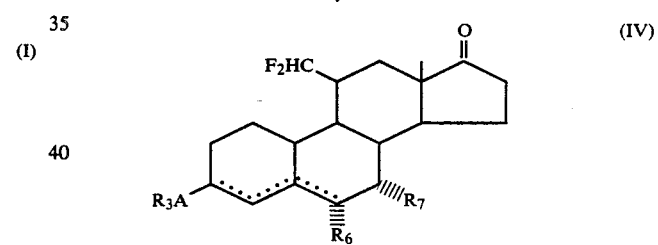
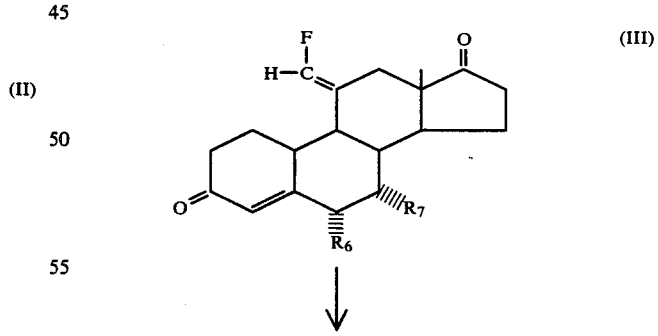
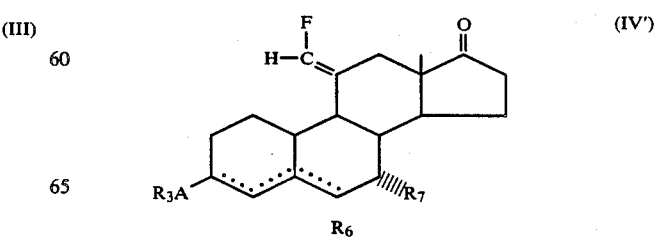

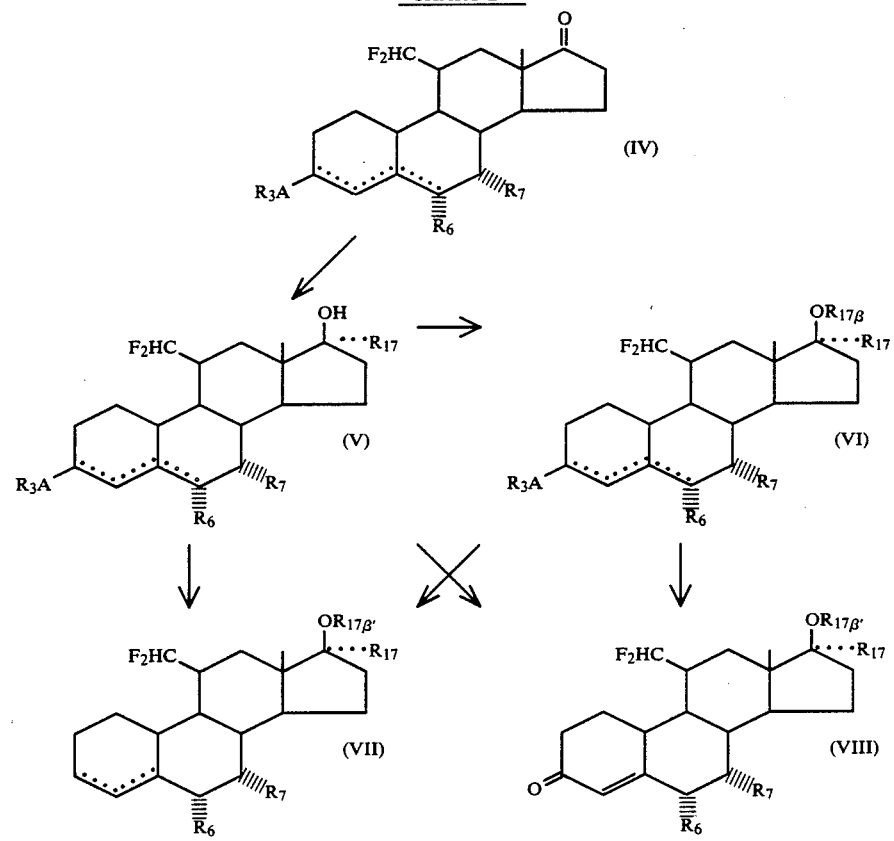
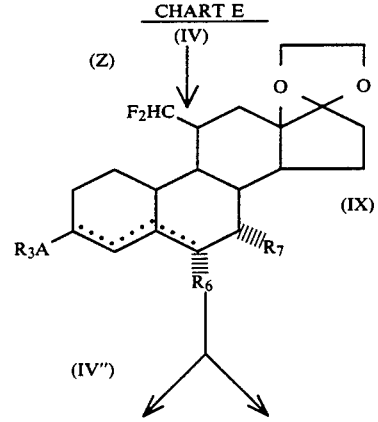
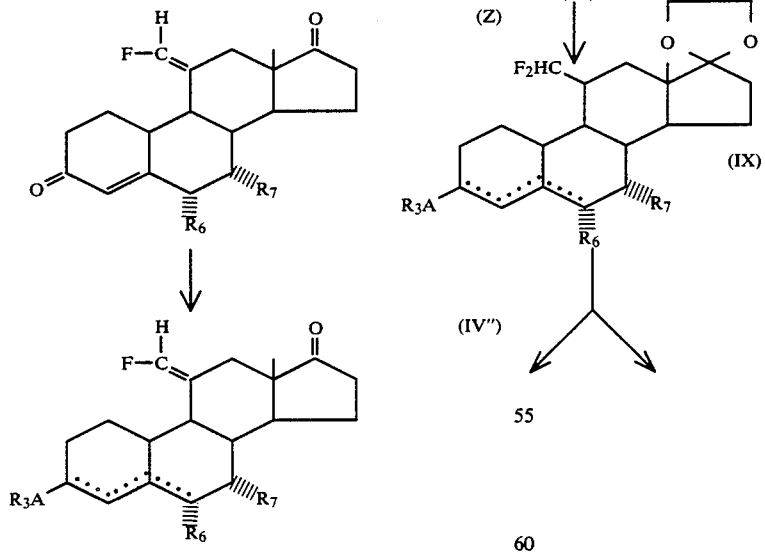

-continued
CHART E
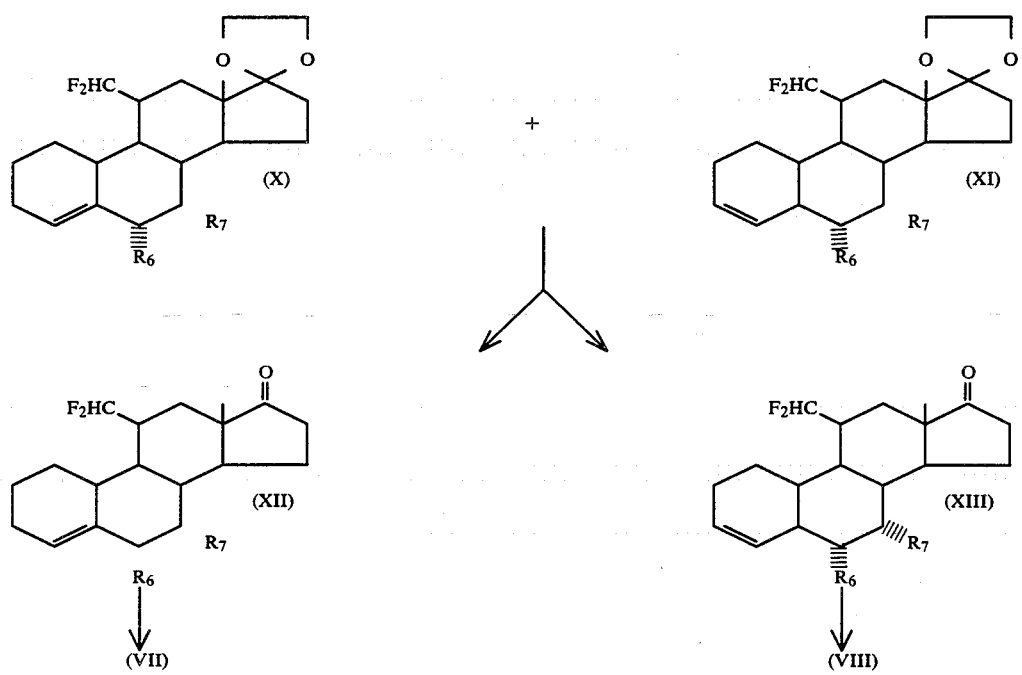
CHART F
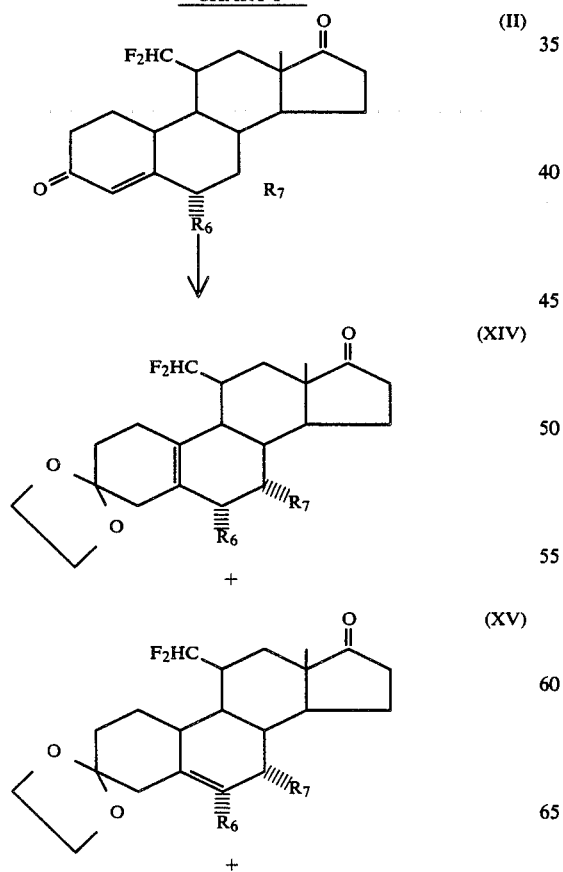
CHART G
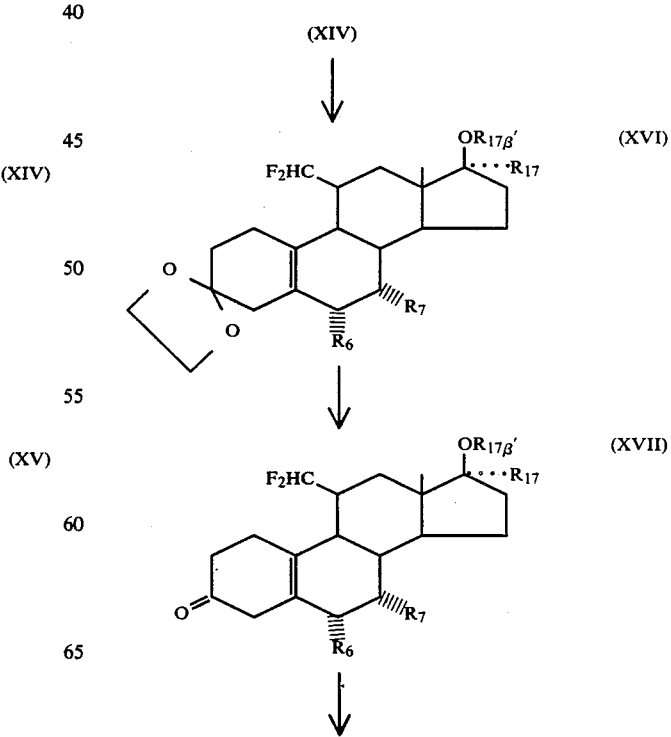

-continued
CHART G
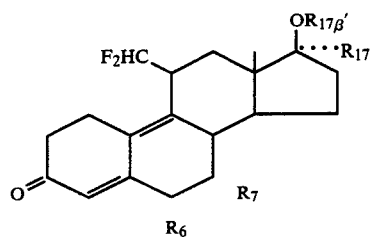
(XVIII)
CHART H
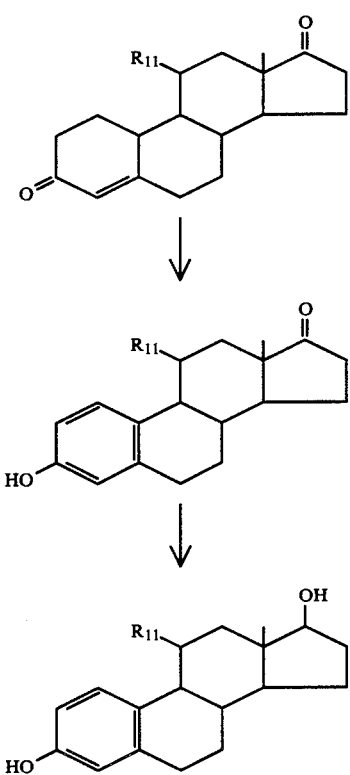
(II, III, Z)
(XIX)
(XX)
CHART I
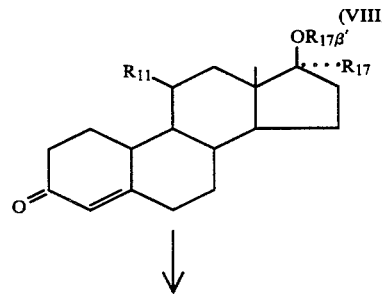
(VIII/VIII'/VIII")
-continued
CHART I
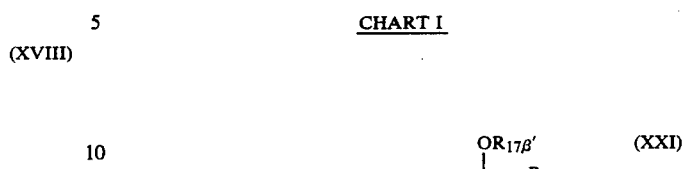
(XXI)
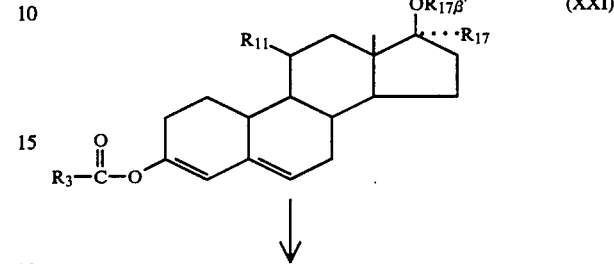
(XXII)
CHART D'
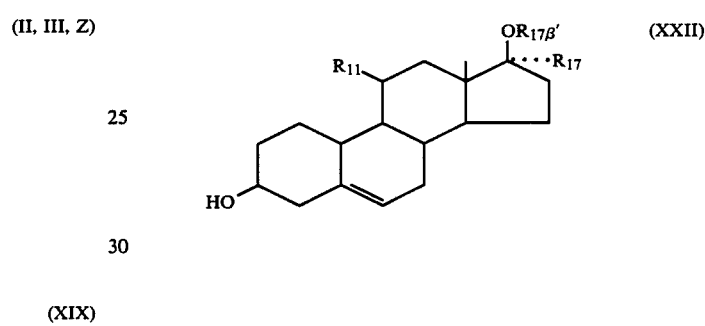
(IV')
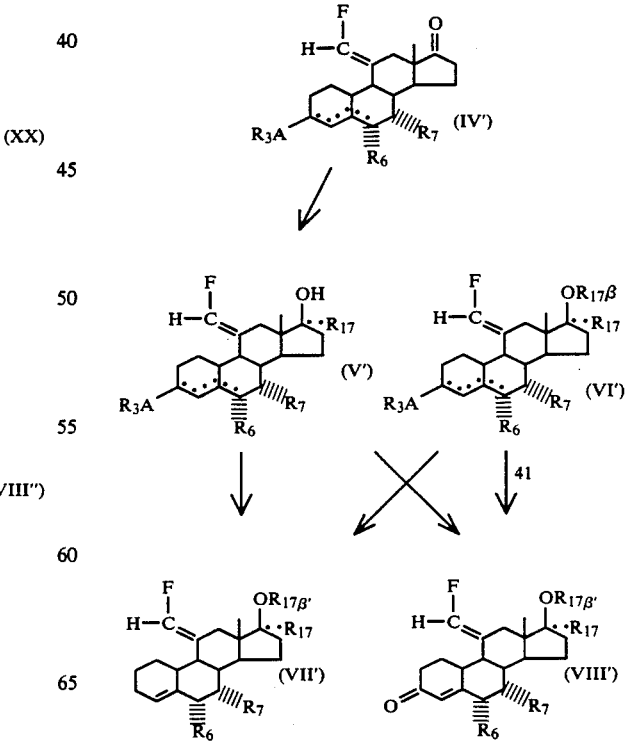
(V') (VI')
(VII') (VIII')

CHART E'
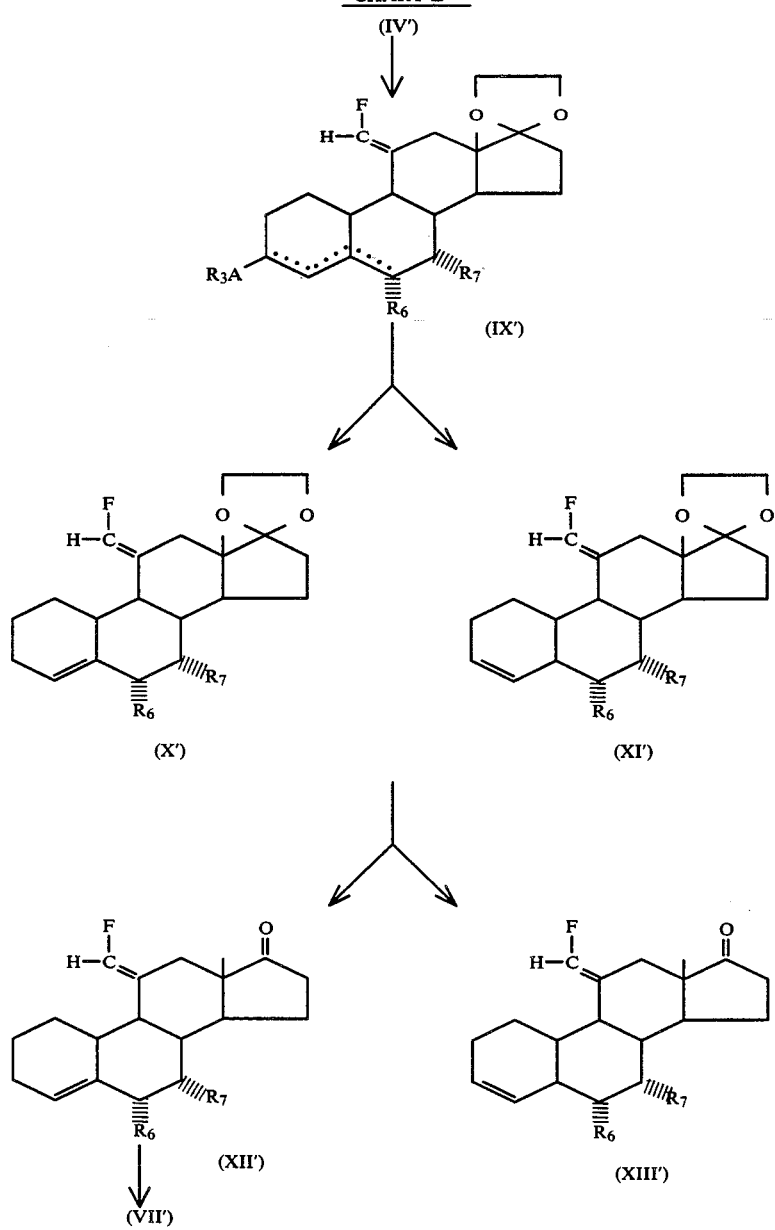
CHART F'
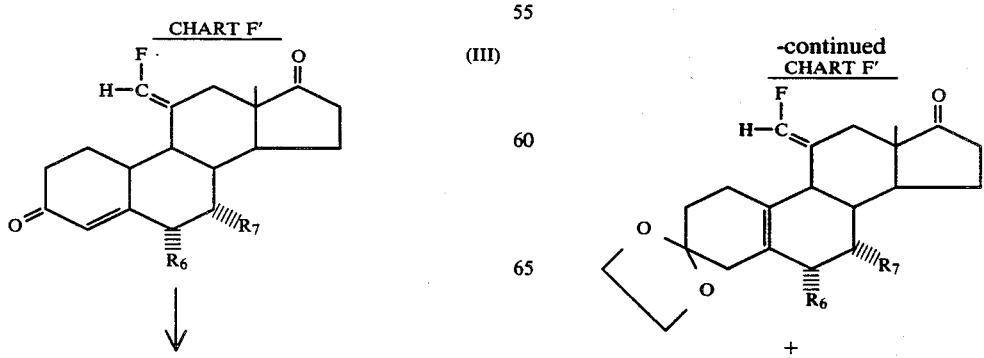

-continued CHART F'
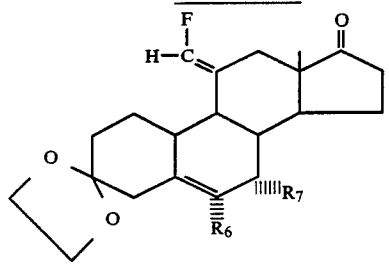 (XV')
CHART G'
(XIV')
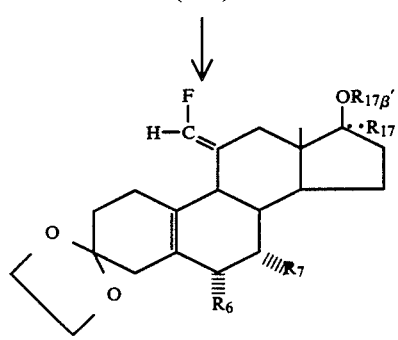 (XVI')
-continued CHART G'
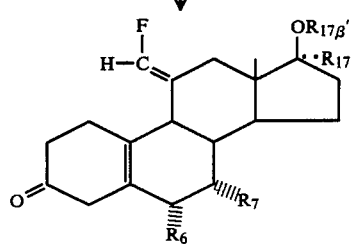 (XVII')
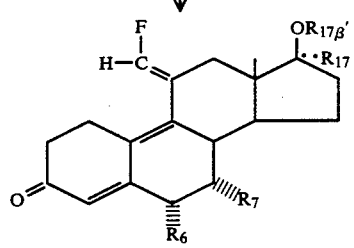 (XVIII')
CHART D''
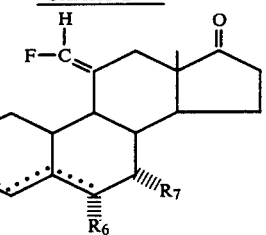 (IV'')
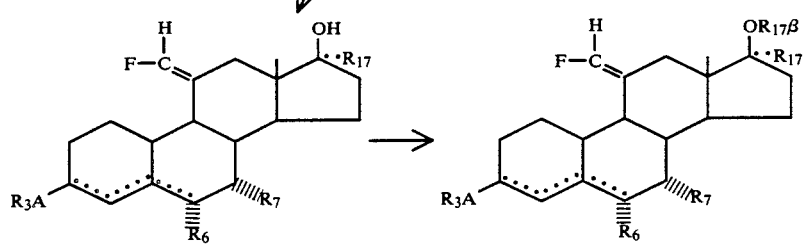
(V'')     (VI'')
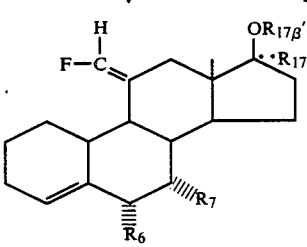 (VII'')
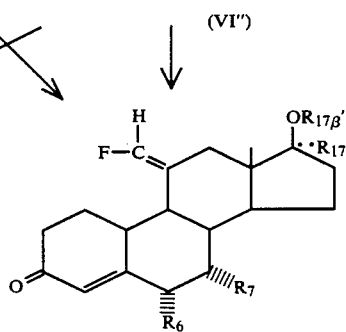 (VIII'')

CHART E''
(IV'')
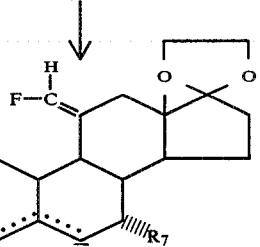
(IX'')
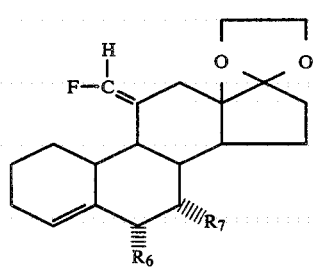
(X'')
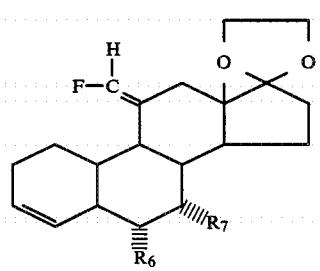
(XI'')
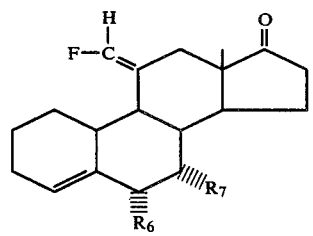
(XII'')
↓
(VII')
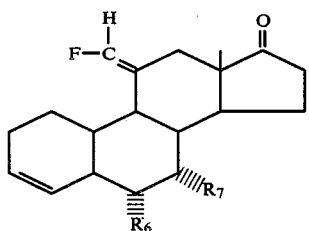
(XIII'')
CHART F''
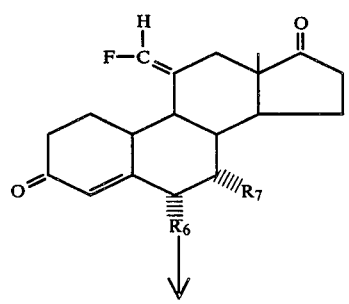
(Z)
-continued
CHART F''
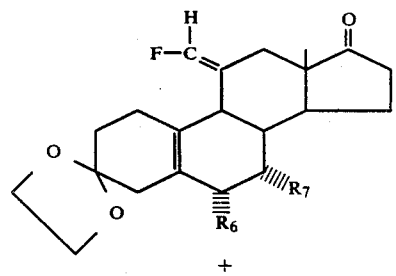
(XIV'')
+

CHART F″
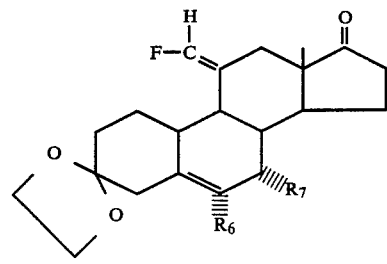
(XV″)
CHART G″
(XIV″)
↓
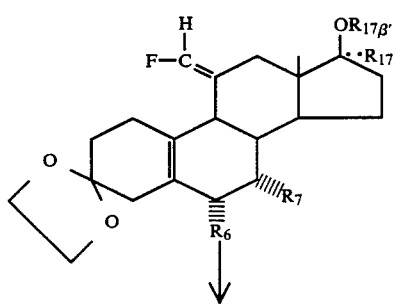
(XVI″)
↓
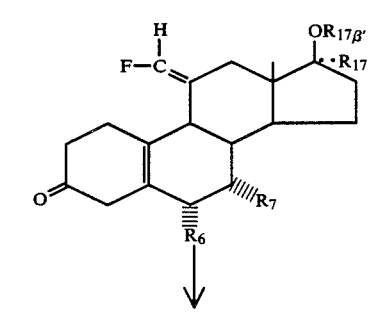
(XVII″)
↓
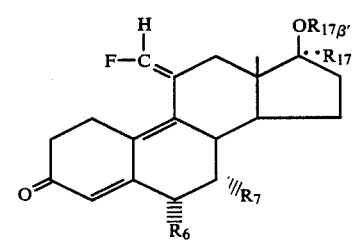
(XVIII″)
CHART A - Et
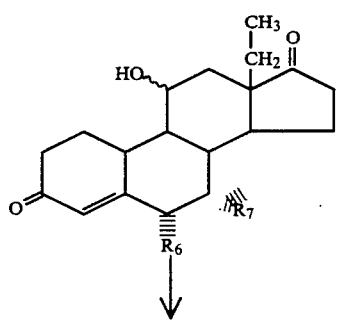
(A-Et)
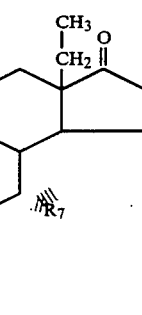
↓
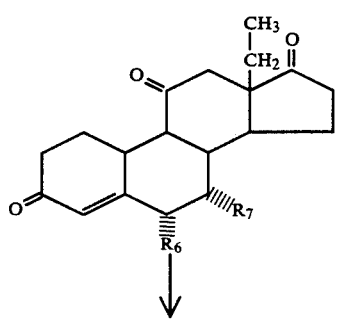
(B-Et)
↓
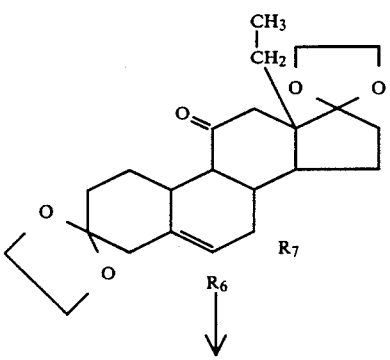
(C-Et)
↓
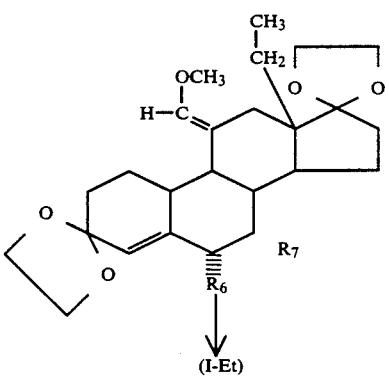
(D-Et)
↓
(I-Et)

51
CHART B - Et
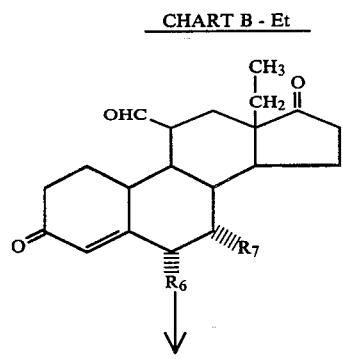
(I-Et)
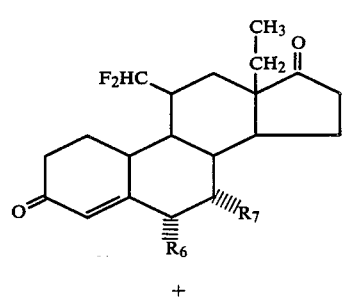
(II-Et)
+
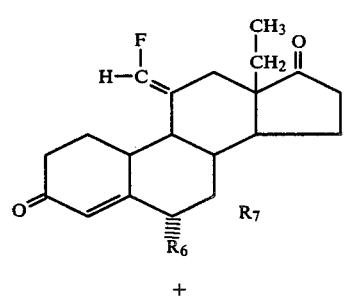
(III-Et)
+
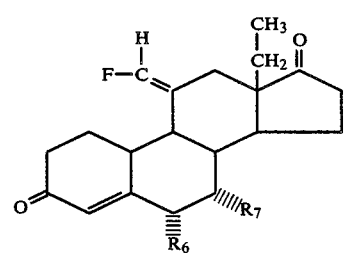
(Z-Et)
CHART C - Et
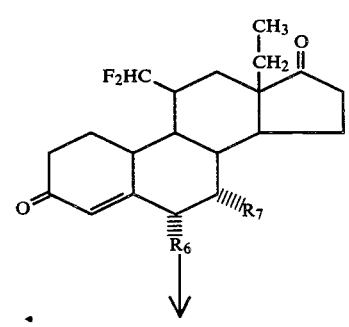
(II-Et)
52
-continued
CHART C - Et
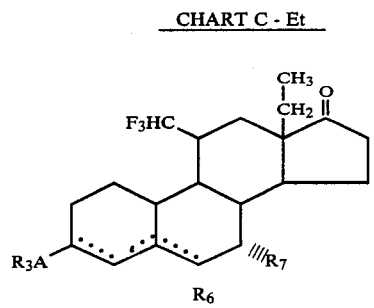
(IV-Et)
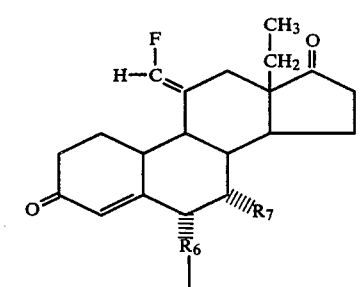
(III-Et)
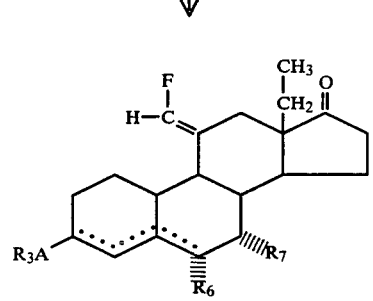
(IV-Et)
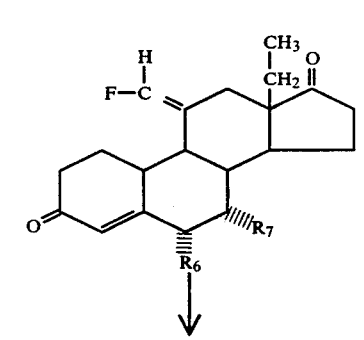
(Z-Et)
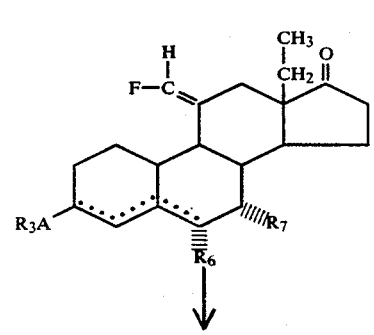
(IV-Et)

4,557,867
CHART D - Et
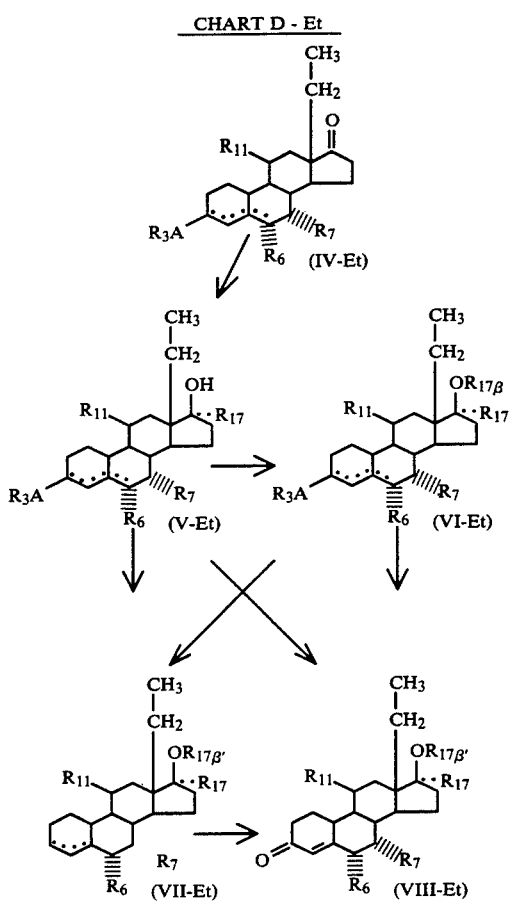
CHART E-Et
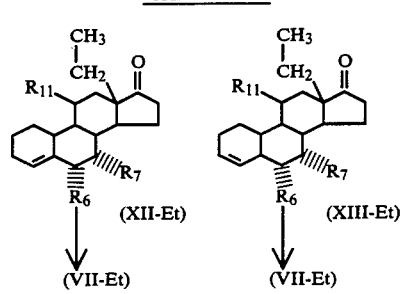
CHART F-Et
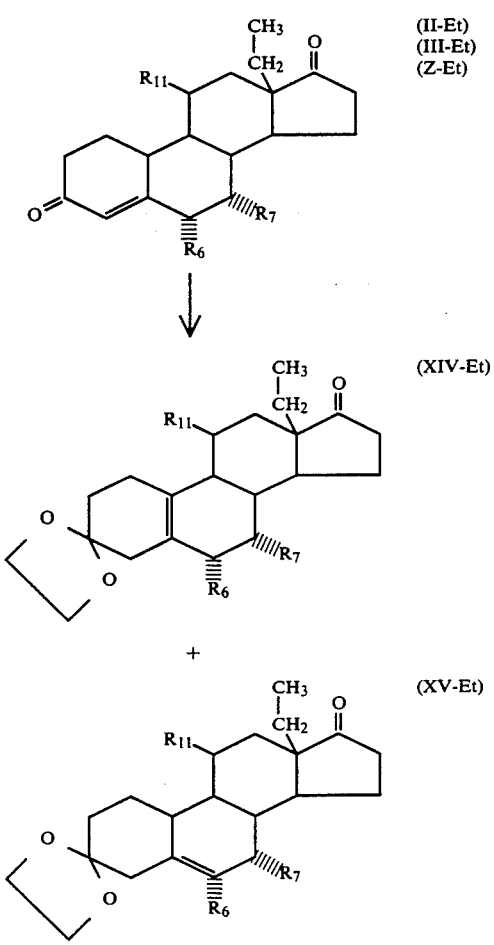
CHART E-Et
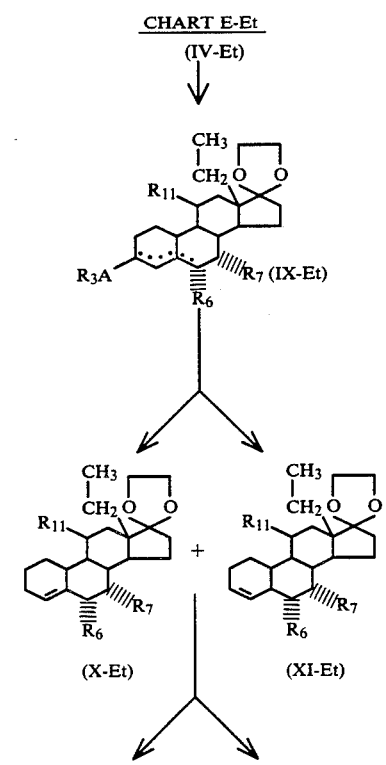
CHART G-Et
(XIV-Et)
↓

-continued
CHART G-Et
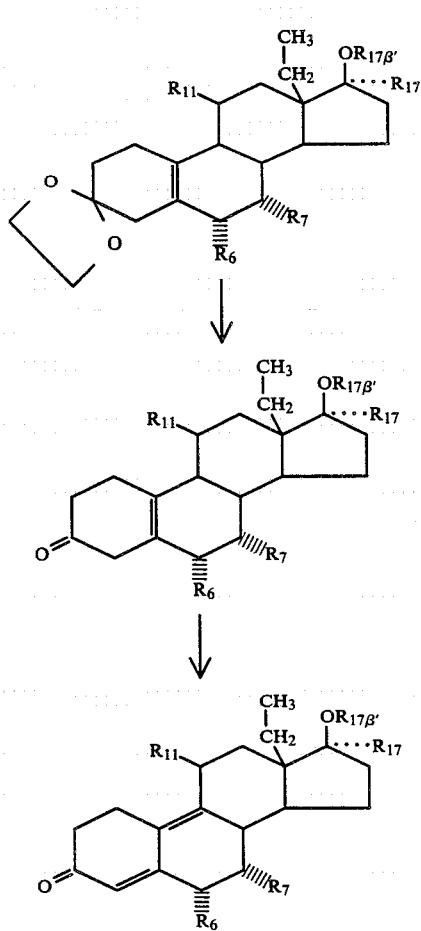
(XVI-Et)
(XVII-Et)
(XVIII-Et)
CHART H-Et
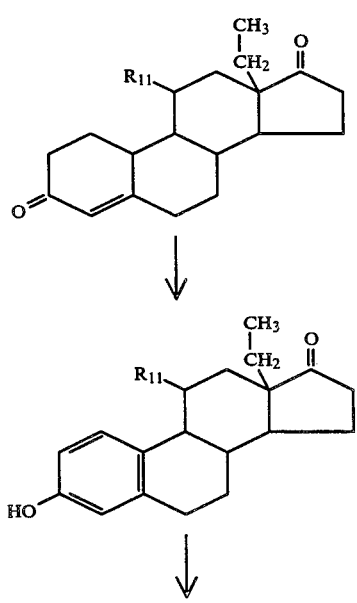
(II-Et)
(III-Et)
(Z-Et)
(XIX-Et)
-continued
CHART H-Et
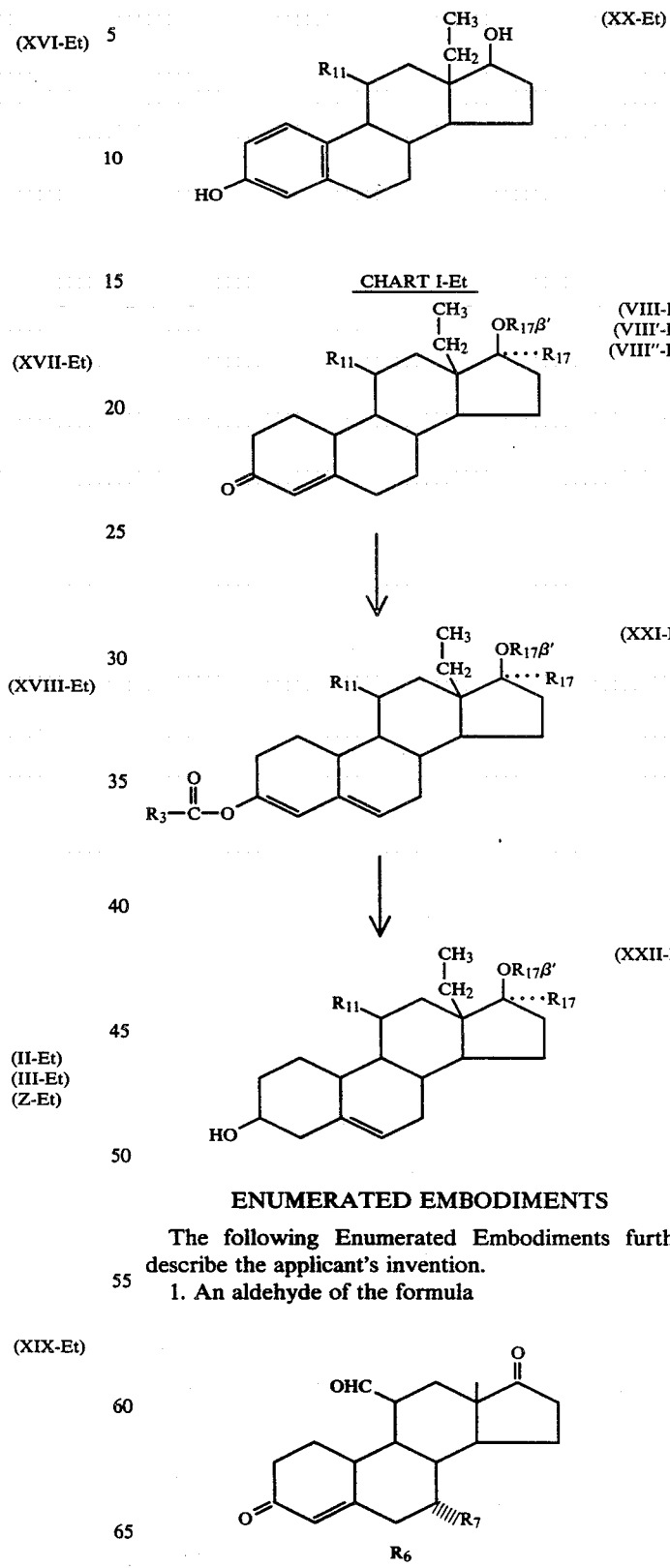
(XX-Et)
CHART I-Et
(VIII-Et)
(VIII'-Et)
(VIII''-Et)
(XXI-Et)
(XXII-Et)
ENUMERATED EMBODIMENTS
The following Enumerated Embodiments further describe the applicant's invention.
1. An aldehyde of the formula
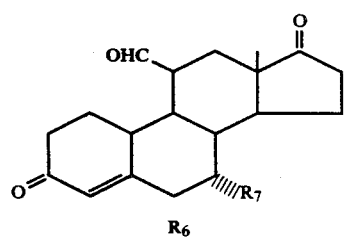
(I)
where R$_6$ is a hydrogen atom or methyl group with the proviso that when R$_6$ is a methyl group, R$_7$ is a hydrogen atom; and R$_7$ is a hydrogen atom or methyl group with the proviso that when R$_7$ is a methyl group, R$_6$ is a hydrogen atom.

2. An aldehyde according to Enumerated Embodiment 1 which is selected from the group consisting of 11$\beta$-formylestr-4-ene-3,17-dione and 11$\beta$-formyl-7$\alpha$-methylestr-4-ene-3,17-dione.

3. A 11$\beta$-difluoromethyl steroid selected from the group consisting of a 11$\beta$-difluoromethyl-17-keto steroid of the formula

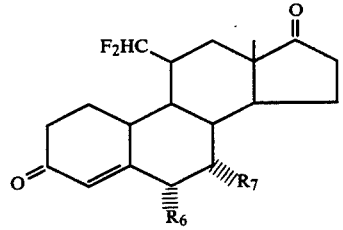
(II)

a C$_3$ protected 11$\beta$-difluoromethyl steroid of the formula

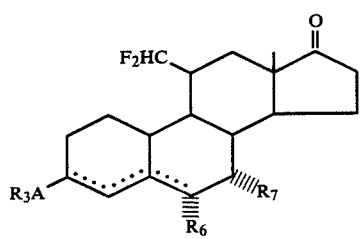
(IV)

and a 3-unsubstituted-17-keto-11$\beta$-difluoromethyl steroid of the formula

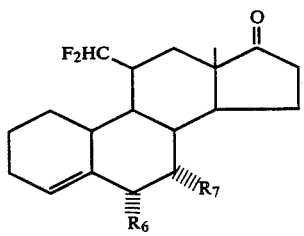
(XII)

where

R$_6$ is a hydrogen atom or methyl group with the proviso that when R$_6$ is a methyl group, R$_7$ is a hydrogen atom; and R$_7$ is a hydrogen atom or methyl group with the proviso that when R$_7$ is a methyl group, R$_6$ is a hydrogen atom.

4. A 11$\beta$-difluoromethyl steroid according to Enumerated Embodiment 3 which is selected from the group consisting of 11$\beta$-difluoromethylestr-4-ene-3,17-dione, 11$\beta$-difluoromethyl-7$\alpha$-methylestr-4-ene-3,17-dione, 11$\beta$-difluoromethylestr-4-ene-3,17-dione 3-ethanedithiol ketal, 11$\beta$-difluoromethyl-7$\alpha$-methylestr-4-ene-3,17-dione 3-ethanedithiol ketal, and 11$\beta$-difluoromethylestr-4-en-17-one.

5. A 11$\beta$-difluoromethyl steroid selected from the group consisting of an 11$\beta$-difluoromethyl steroid of the formula

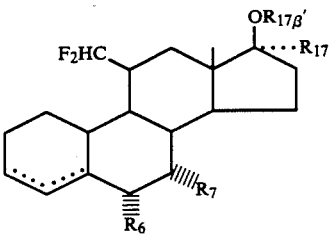
(VII)

a $\Delta^4$-3-keto 11$\beta$-difluoromethyl steroid of the formula,

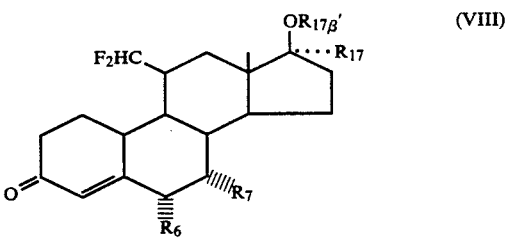
(VIII)

a $\Delta^{5(10)}$-3-keto-11$\beta$-difluoromethyl steroid of the formula,

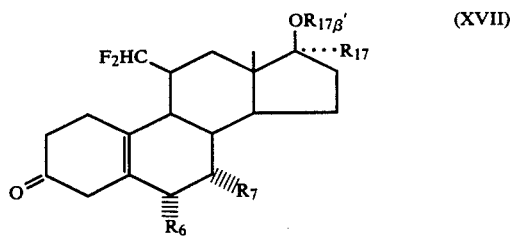
(XVII)

and a $\Delta^{4,9}$-11$\beta$-difluoromethyl steroid of the formula

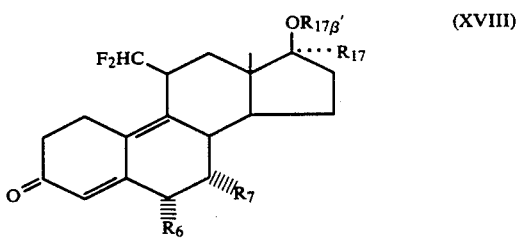
(XVIII)

where

R$_6$ is a hydrogen atom or methyl group with the proviso that when R$_6$ is a methyl group, R$_7$ is a hydrogen atom;

R$_7$ is a hydrogen atom or methyl group with the proviso that when R$_7$ is a methyl group, R$_6$ is a hydrogen atom;

R$_{17}$ is a hydrogen atom, alkyl of 1 through 4 carbon atoms, —C≡C—R$_{17A}$, —CH=CH—R$_{17B}$;

R$_{17A}$ is a hydrogen atom, methyl or ethyl group or trifluoromethyl;

R$_{17B}$ is a hydrogen atom, methyl or ethyl group or —CH=CH$_2$ group;

R$_{17\beta'}$ is a hydrogen atom or R$_{17\beta}$;

$R_{17\beta}$ is alkyl of 1 through 4 carbon atoms and OCO—$R_{17C}$;

$R_{17C}$ is alkyl of 1 through 6 carbon atoms, cyclopentylethyl and phenyl.

6. A 11β-difluoromethyl steroid according to Enumerated Embodiment 5 where $R_{17}$ is selected from the group consisting of a hydrogen atom, methyl, ethynyl or propynyl group.

7. A 11β-difluoromethyl steroid according to Enumerated Embodiment 5 where $R_{17\beta'}$ is selected from the group consisting of a hydrogen atom, methyl or acetyl group.

8. A 11β-difluoromethyl steroid according to Enumerated Embodiment 5 which is selected from the group consisting of 17α-ethynyl-11β-difluoromethyl-17β-hydroxyestr-4-ene, 11β-difluoromethyl-17β-hydroxy-17α-propynylestr-4-ene, 17α-ethynyl-11β-difluoromethyl-17β-hydroxyestr-4-en-3-one, 11β-difluoromethyl-17β-hydroxy-17α-propynylestr-4-en-3-one, 17α-ethynyl-11β-difluoromethyl-17β-hydroxyestr-4-en-3-one 17-methyl ether, 11β-difluoromethyl-17β-hydroxy-7α-methyl-17α-propynylestr-4-en-3-one, 17α-ethynyl-11β-difluoromethyl-17α-hydroxy-7α-methylestr-4-en-3-one, 17α-ethynyl-11β-difluoromethyl-17β-hydroxyestr-4-en-3-one 17-acetate, 11β-difluoromethyl-17β-hydroxy-17α-propynylestr-4-en-3-one 17-acetate, 11β-difluoromethyl-17β-hydroxy-17α-propynylestr-4-en-3-one 17-methyl ether, 11β-difluoromethyl-17β-hydroxyestr-4-en-3-one 17-methyl ether, 11β-difluoromethyl-17β-hydroxyestr-4-en-3-one, 17α-ethynyl-11β-difluoromethyl-17β-hydroxyestr-5(10)-en-3-one, and 17α-ethynyl-11β-difluoromethyl-17β-hydroxyestra-4,9-dien-3-one.

9. A (E)-11-fluoromethylene steroid selected from the group consisting of a (E)-11-fluoromethylene-17-keto steroid of the formula

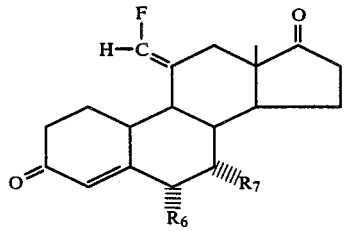
(III)

a $C_3$ protected (E)-11-fluoromethylene steroid of the formula

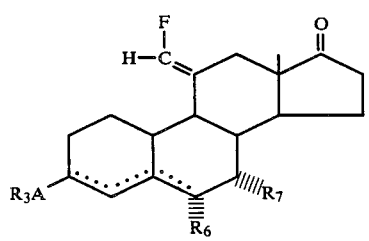
(IV')

and a 3-unsubstituted-17-keto-(E)-11-fluoromethylene steroid of the formula

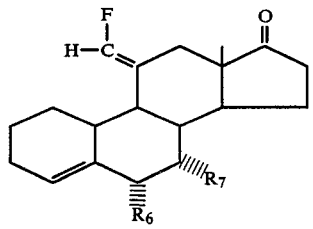
(XII')

where $R_6$ is a hydrogen atom or methyl group with the proviso that when $R_6$ is a methyl group, $R_7$ is a hydrogen atom; and $R_7$ is a hydrogen atom or methyl group with the proviso that when $R_7$ is a methyl group, $R_6$ is a hydrogen atom.

10. A (E)-11-fluoromethylene steroid according to Enumerated Embodiment 9 which is selected from the group consisting of (E)-11-(-fluoromethylene)estr-4-ene-3,17-dione, (E)-11-fluoromethylene-7α-methylestr-4-ene-3,17-dione, (E)-11-(fluoromethylene)estr-4-ene-3,17-dione 3-ethanedithiol ketal, and (E)-11-fluoromethylene-7α-methylestr-4-ene-3,17-dione 3-ethanedithiol ketal.

11. A (E)-11-fluoromethylene steroid selected from the group consisting of a (E)-11-fluoromethylene steroid of the formula

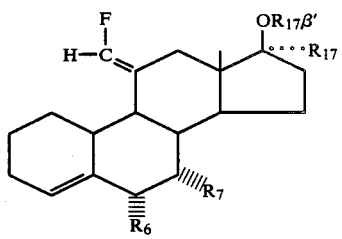
(VII')

a Δ⁴-3-keto (E)-11-fluoromethylene steroid of the formula,

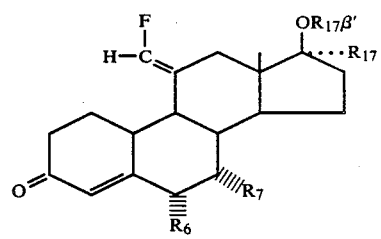
(VIII')

a Δ⁵⁽¹⁰⁾-3-keto-(E)-11-fluoromethylene steroid of the formula,

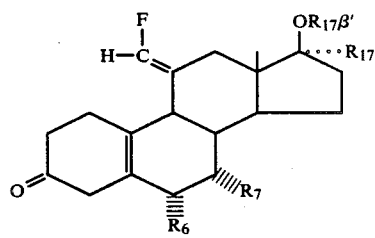
(XVII')

and a Δ⁴,⁹-(E)-11-fluoromethylene steroid of the formula

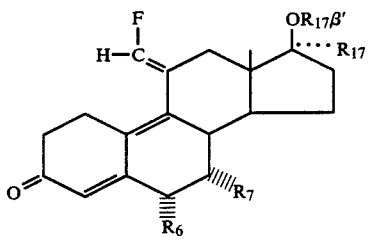

(XVIII')

where
R₆ is a hydrogen atom or methyl group with the proviso that when R₆ is a methyl group, R₇ is a hydrogen atom;
R₇ is a hydrogen atom or methyl group with the proviso that when R₇ is a methyl group, R₆ is a hydrogen atom;
R₁₇ is a hydrogen atom, alkyl of 1 through 4 carbon atoms, —C≡C—R₁₇ₐ, —CH=CH—R₁₇ᵦ; and
R₁₇ₐ is a hydrogen atom, methyl or ethyl group or trifluoromethyl;
R₁₇ᵦ is a hydrogen atom, methyl or ethyl group or —CH=CH₂ group;
R₁₇β' is a hydrogen atom or R₁₇β;
R₁₇β is alkyl of 1 through 4 carbon atoms and OCO—R₁₇C;
R₁₇C is alkyl of 1 through 6 carbon atoms, cyclopentylethyl and phenyl.

12. A (E)-11-fluoromethylene steroid according to Enumerated Embodiment 11 where R₁₇ is selected from the group consisting of a hydrogen atom, methyl, ethynyl or propynyl group.

13. A (E)-11-fluoromethylene steroid according to Enumerated Embodiment 11 where R₁₇β' is selected from the group consisting of a hydrogen atom, methyl or acetyl group.

14. A (E)-11-fluoromethylene steroid according to Enumerated Embodiment 11 which is selected from the group consisting of 17α-ethynyl-(E)-11-(fluoromethylene)estr-4-ene, 17α-ethynyl-(E)-11-fluoromethylene-17β-hydroxyestr-4-en-3-one, (E)-11-fluoromethylene-17β-hydroxy-17α-propynylestr-4-en-3-one, 17α-ethynyl-(E)-11-fluoromethylene-17α-hydroxy-7α-methylestr-4-en-3-one, (E)-11-fluoromethylene-17β-hydroxy-7α-methyl-17α-propynylestr-4-en-3-one, and (E)-11-fluoromethylene-17β-hydroxy-17α-propynylestr-4-en-3-one 17-methyl ether.

15. 7α-Methylestr-4-ene-3,11,17-trione.

16. A (Z)-11-fluoromethylene steroid selected from the group consisting of a (Z)-11-fluoromethylene-17-keto steroid of the formula

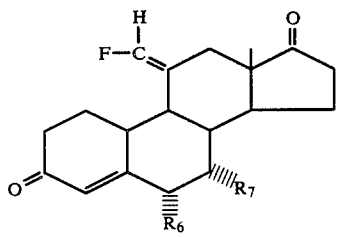

(Z)

a C₃ protected (Z)-11-fluoromethylene steroid of the formula

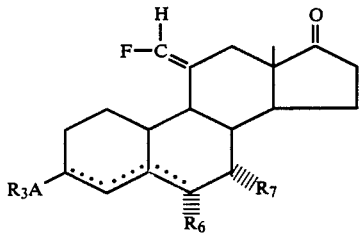

(IV'')

and a 3-unsubstituted-17-keto-(Z)-11-fluoromethylene steroid of the formula

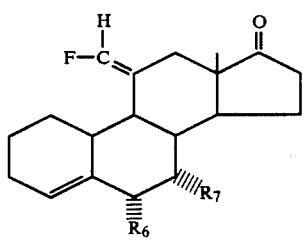

(XII'')

where
R₆ is a hydrogen atom or methyl group with the proviso that when R₆ is a methyl group, R₇ is a hydrogen atom; and
R₇ is a hydrogen atom or methyl group with the proviso that when R₇ is a methyl group, R₆ is a hydrogen atom.

17. A (Z)-11-fluoromethylene steroid according to Enumerated Embodiment 16 which is (Z)-11-(fluoromethylene)estr-4-ene-3,17-dione.

18. A (Z)-11-fluoromethylene steroid selected from the group consisting of a (Z)-11-fluoromethylene steroid of the formula

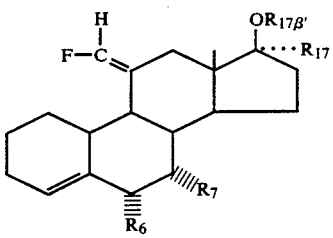

(VII'')

a Δ⁴-3-keto (Z)-11-fluoromethylene steroid of the formula,

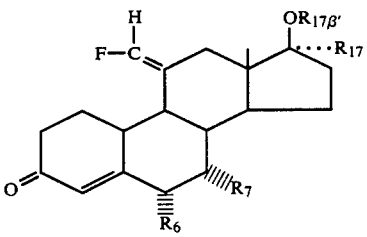

(VIII'')

a Δ⁵⁽¹⁰⁾-3-keto-(Z)-11-fluoromethylene steroid of the formula,

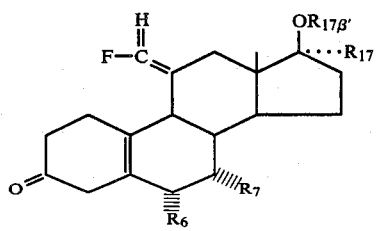
(XVII″)

and a Δ$^{4,9}$-(Z)-11-fluoromethylene steroid of the formula

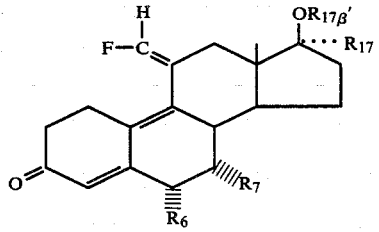
(XVIII″)

where
- R$_6$ is a hydrogen atom or methyl group with the proviso that when R$_6$ is a methyl group, R$_7$ is a hydrogen atom;
- R$_7$ is a hydrogen atom or methyl group with the proviso that when R$_7$ is a methyl group, R$_6$ is a hydrogen atom;
- R$_{17}$ is a hydrogen atom, alkyl of 1 through 4 carbon atoms, —C≡C—R$_{17A}$, —CH=CH—R$_{17B}$; and
- R$_{17A}$ is a hydrogen atom, methyl or ethyl group or trifluoromethyl;
- R$_{17B}$ is a hydrogen atom, methyl or ethyl group or —CH=CH$_2$ group;
- R$_{17\beta}'$ is a hydrogen atom or R$_{17\beta}$;
- R$_{17\beta}$ is alkyl of 1 through 4 carbon atoms and OCO—R$_{17C}$;
- R$_{17C}$ is alkyl of 1 through 6 carbon atoms, cyclopentylethyl and phenyl.

19. A (Z)-11-fluoromethylene steroid according to Enumerated Embodiment 18 where R$_{17}$ is selected from the group consisting of a hydrogen atom, methyl, ethynyl or propynyl group.

20. A (Z)-11-fluoromethylene steroid according to Enumerated Embodiment 18 where R$_{17\beta}'$ is selected from the group consisting of a hydrogen atom, methyl or acetyl group.

21. A (Z)-11-fluoromethylene steroid according to Enumerated Embodiment 18 which is selected from the group consisting of 17α-ethynyl-(Z)-11-fluoromethylene-17β-hydroxyestr-4-en-3-one and (Z)-11-fluoromethylene-17β-hydroxy-17α-propynylestr-4-en-3-one.

22. A 13β-ethyl steroid selected from the group consisting of 13β-ethyl-11β-difluoromethyl steroid of the formula 13β-ethyl-(E)-11-fluoromethylene steroids of the formula

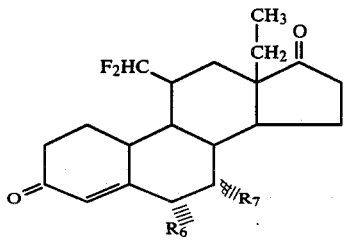
(II-Et)

13β-ethyl-(Z)-11-fluoromethylene steroids of the formula

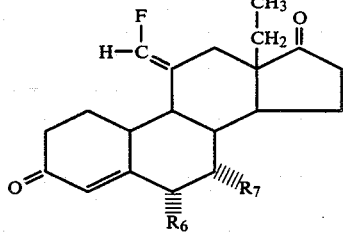
(III-Et)

13β-ethyl-(Z)-11-fluoromethylene steroids of the formula

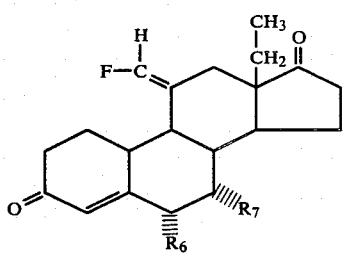
(Z-Et)

13β-ethyl-C$_3$-protected steroids of the formula

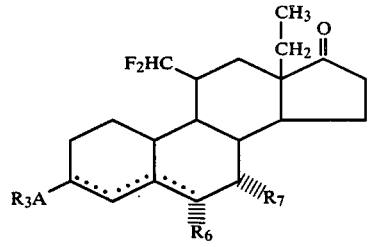
(IV-Et)

and 13β-ethyl-3-unsubstituted-17-keto steroids of the formula

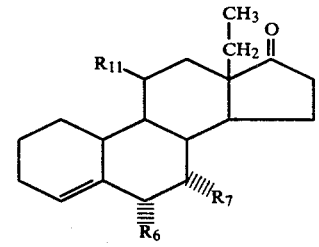
(XII-Et)

where $R_6$ is a hydrogen atom or methyl group with the proviso that when $R_6$ is a methyl group, $R_7$ is a hydrogen atom;

$R_7$ is a hydrogen atom or methyl group with the proviso that when $R_7$ is a methyl group, $R_6$ is a hydrogen atom;

$R_{11}$ refers to a difluoromethyl, (E)-fluoromethylene or (Z)-fluoromethylene group.

23. A 13β-ethyl steroid according to Enumerated Embodiment 22 which is selected from the group consisting of 13β-ethyl-11β-difluoromethylgon-4-ene-3,17-dione, 13β-ethyl-(E)-11-fluoromethylenegon-4-ene-3,17-dione, 13β-ethyl-(Z)-11-fluoromethylenegon-4-ene-3,17-dione.

24. A 13β-ethyl steroid selected from the group consisting of 13β-ethyl-3-unsubstituted steroid of the formula

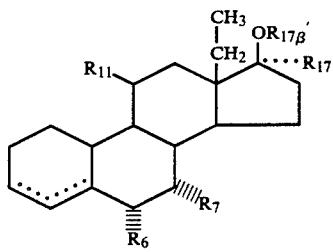

(VII-Et)

a 13β-ethyl-Δ⁴-3-keto steroid of the formula

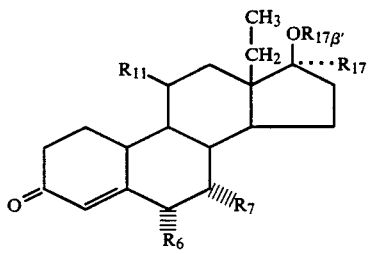

(VIII-Et)

a 13β-ethyl-Δ⁵(¹⁰)-3-keto steroid of the formula

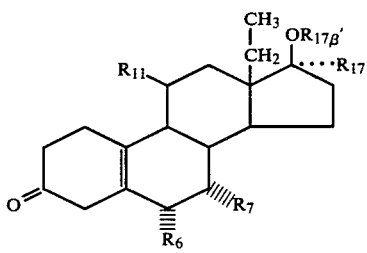

(XVII-Et)

and a 13β-ethyl-Δ⁴,⁹-steroid of the formula

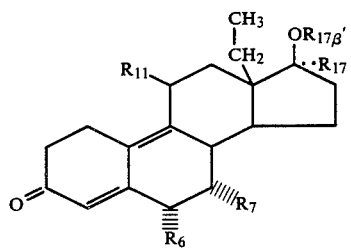

(XVIII-Et)

where $R_6$ is a hydrogen atom or methyl group with the proviso that when $R_6$ is a methyl group, $R_7$ is a hydrogen atom;

$R_7$ is a hydrogen atom or methyl group with the proviso that when $R_7$ is a methyl group, $R_6$ is a hydrogen atom;

$R_{11}$ refers to a difluoromethyl, (E)-fluoromethylene or (Z)-fluoromethylene group;

$R_{17}$ is a hydrogen atom, alkyl of 1 through 4 carbon atoms, —C≡C—$R_{17A}$, —CH=CH—$R_{17B}$; and $R_{17A}$ is a hydrogen atom, methyl or ethyl group or trifluoromethyl;

$R_{17B}$ is a hydrogen atom, methyl or ethyl group or —CH=CH$_2$ group;

$R_{17β}'$ is a hydrogen atom or $R_{17β}$;

$R_{17β}$ is alkyl of 1 through 4 carbon atoms and OCO—$R_{17C}$;

$R_{17C}$ is alkyl of 1 through 6 carbon atoms, cyclopentylethyl and phenyl.

25. A 13β-ethyl steroid according to Enumerated Embodiment 22 where $R_{17}$ is selected from the group consisting of a hydrogen atom, methyl, ethynyl or propynyl group.

26. A 13β-ethyl steroid according to Enumerated Embodiment 22 where $R_{17β}'$ is selected from the group consisting of a hydrogen atom, methyl or acetyl group.

27. A 13β-ethyl steroid according to Enumerated Embodiment 22 which is selected from the group consisting of 13β-ethyl-(Z)-11-fluoromethylene-17β-hydroxy-17α-propynylgon-4-en-3-one, 13β-ethyl-17α-ethynyl-(E)-11-fluoromethylene-17β-hydroxygon-4-en-3-one, 13β-ethyl-(E)-11-fluoromethylene-17β-hydroxy-17α-propynylgon-4-en-3-one and 13β-ethyl-11β-difluoromethyl-17β-hydroxy-17α-propynylgon-4-en-3-one.

28. A (E)-11-fluoromethylene steroid according to Enumerated Embodiment 9 which is (E)-11-(fluoromethylene)estr-4-en-17-one.

29. A (E)-11-fluoromethylene steroid according to Enumerated Embodiment 11 which is selected from the group consisting of (E)-11-fluoromethylene-17β-hydroxy-17α-methylestr-4-en-3-one, (E)-11-fluoromethylene-17β-hydroxyestr-4-en-3-one, (E)-11-fluoromethylene-17β-hydroxyestr-4-en-3-one 17-acetate, (E)-11-fluoromethylene-17β-hydroxy-17α-propynylestr-4-ene and 17α-ethynyl-17β-hydroxy-(E)-11-fluoromethyleneestr-4-ene.

30. A steroid selected from the group consisting of 11-substituted estrone

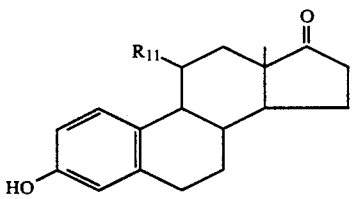

(XIX)

3-acyloxy

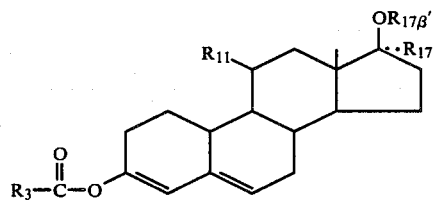

13β-ethyl-11-substituted estrone

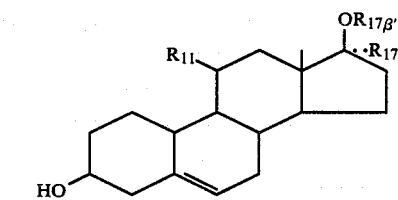

13β-ethyl-11-substituted estradiol

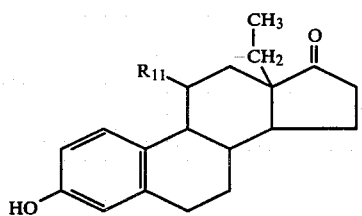

and 13β-ethyl-3-acyloxy

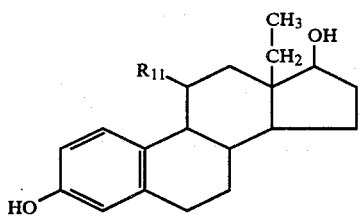

and 13β-ethyl-3β-hydroxy

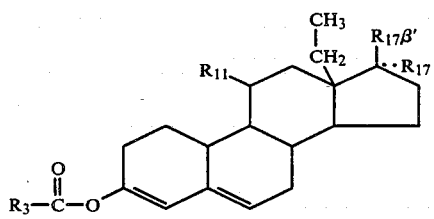

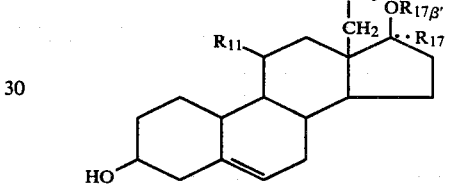

where
- $R_3$ is alkyl of 1 thru 5 carbon atoms or phenyl;
- $R_{11}$ refers to a difluoromethyl, (E)-fluoromethylene or (Z)-fluoromethylene group;
- $R_{17}$ is a hydrogen atom, alkyl of 1 through 4 carbon atoms, —C≡C—$R_{17A}$, —CH=CH—$R_{17B}$; and
- $R_{17A}$ is a hydrogen atom, methyl or ethyl group or trifluoromethyl;
- $R_{17B}$ is a hydrogen atom, methyl or ethyl group or —CH=CH$_2$ group;
- $R_{17\beta'}$ is a hydrogen atom or $R_{17\beta}$;
- $R_{17\beta}$ is alkyl of 1 through 4 carbon atoms and OCO—$R_{17C}$;
- $R_{17C}$ is alkyl of 1 through 6 carbon atoms, cyclopentylethyl and phenyl.

31. A steroid according to Enumerated Embodiment 30 which is (E)-11-(fluoromethylene)estrone.

32. A steroid selected from the group consisting of 11-substituted estradiol

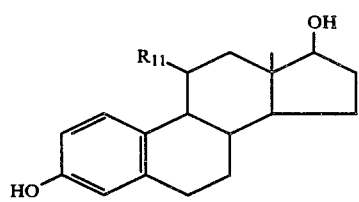

3β-hydroxy where
- $R_{11}$ refers to a difluoromethyl, (E)-fluoromethylene or (Z)-fluoromethylene group;
- $R_{17}$ is a hydrogen atom, alkyl of 1 through 4 carbon atoms, —C≡C—$R_{17A}$, —CH=CH—$R_{17B}$; and
- $R_{17A}$ is a hydrogen atom, methyl or ethyl group or trifluoromethyl;
- $R_{17B}$ is a hydrogen atom, methyl or ethyl group or —CH=CH$_2$ group;
- $R_{17\beta'}$ is a hydrogen atom or $R_{17\beta}$;
- $R_{17\beta}$ is alkyl of 1 through 4 carbon atoms and OCO—$R_{17C}$;
- $R_{17C}$ is alkyl of 1 through 6 carbon atoms, cyclopentylethyl and phenyl.

33. A steroid according to Enumerated Embodiment 32 where $R_{17}$ is selected from the group consisting of a hydrogen atom, methyl, ethynyl or propynyl group.

34. A steroid according to Enumerated Embodiment 32 where $R_{17\beta'}$ is selected from the group consisting of a hydrogen atom, methyl or acetyl group.

35. A steroid according to Enumerated Embodiment 32 which is selected from the group consisting of (E)-11-(fluoromethylene)estradiol and (E)-11-(fluoromethylene)-3β,17β-dihydroxy-17α-propynylestr-5-ene.

I claim:

1. A 11β-difluoromethyl steroid selected from the group consisting of a 3-unsubstituted-11β-difluoromethyl steroid of the formula

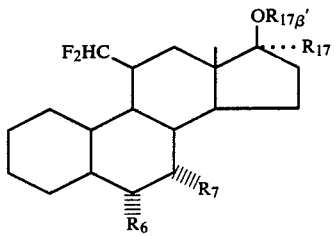

a $\Delta^4$-3-keto 11β-difluoromethyl steroid of the formula,

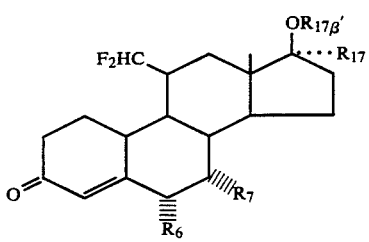

a $\Delta^{5(10)}$-3-keto-11β-difluoromethyl steroid of the formula,

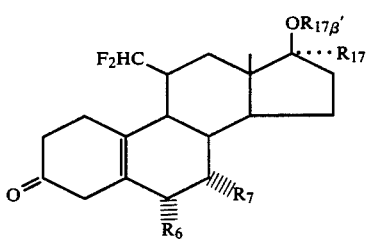

and a $\Delta^{4,9}$-11β-difluoromethyl steroid of the formula

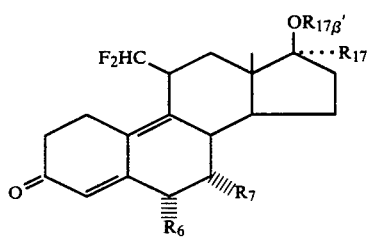

where
- $R_6$ is a hydrogen atom or methyl group with the proviso that when $R_6$ is a methyl group, $R_7$ is a hydrogen atom;
- $R_7$ is a hydrogen atom or methyl group with the proviso that when $R_7$ is a methyl group, $R_6$ is a hydrogen atom;
- $R_{17}$ is a hydrogen atom, alkyl of 1 through 4 carbon atoms, —C≡C—$R_{17A}$, —CH=CH—$R_{17B}$;
- $R_{17A}$ is a hydrogen atom, methyl or ethyl group or trifluoromethyl;
- $R_{17B}$ is a hydrogen atom, methyl or ethyl group or —CH=CH$_2$ group;
- $R_{17\beta'}$ is a hydrogen atom or $R_{17\beta}$;
- $R_{17\beta}$ is alkyl of 1 through 4 carbon atoms and OCO—$R_{17C}$;
- $R_{17C}$ is alkyl of 1 through 6 carbon atoms, cyclopentylethyl and phenyl.

2. A 11β-difluoromethyl steroid according to claim 1 where $R_{17}$ is selected from the group consisting of a hydrogen atom, methyl, ethynyl or propynyl group.

3. A 11β-difluoromethyl steroid according to claim 1 where $R_{17\beta'}$ is selected from the group consisting of a hydrogen atom, methyl or acetyl group.

4. A 11β-difluoromethyl steroid according to claim 1 which is selected from the group consisting of 17α-ethynyl-11β-difluoromethyl-17β-hydroxyestr-4-ene, 11β-difluoromethyl-17β-hydroxy-17α-propynylestr-4-ene, 17α-ethynyl-11β-difluoromethyl-17β-hydroxyestr-4-en-3-one, 11β-difluoromethyl-17β-hydroxy-17α-propynylestr-4-en-3-one, 17α-ethynyl-11β-difluoromethyl-17β-hydroxyestr-4-en-3-one 17-methyl ether, 11β-difluoromethyl-17β-hydroxy-7α-methyl-17α-propynylestr-4-en-3-one, 17α-ethynyl-11β-difluoromethyl-17α-hydroxy-7α-methylestr-4-en-3-one, 17α-ethynyl-11β-difluoromethyl-17β-hydroxyestr-4-en-3-one 17-acetate, 11β-difluoromethyl-17β-hydroxy-17α-propynylestr-4-en-3-one 17-acetate, 11β-difluoromethyl-17β-hydroxy-17α-propynylestr-4-en-3-one 17-methyl ether, 11β-difluoromethyl-17β-hydroxyestr-4-en-3-one 17-methyl ether, 11β-difluoromethyl-17β-hydroxyestr-4-en-3-one, 17α-ethynyl-11β-difluoromethyl-17β-hydroxyestr-5(10)-en-3-one, and 17α-ethynyl-11β-difluoromethyl-17β-hydroxyestra-4,9-dien-3-one.

5. A (E)-11-fluoromethylene steroid selected from the group consisting of a (E)-11-fluoromethylene-17-keto steroid of the formula

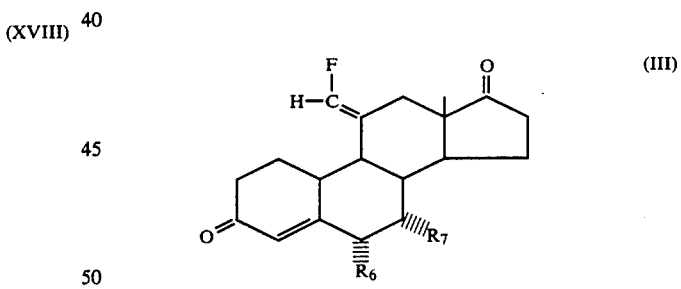

a $C_3$ protected (E)-11-fluoromethylene steroid of the formula

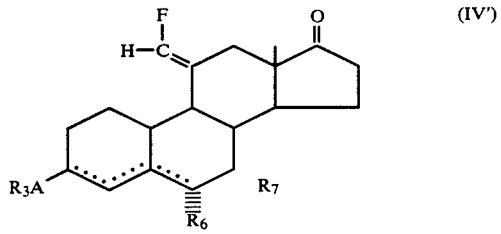

and a 3-unsubstituted-17-keto-(E)-11-fluoromethylene steroid of the formula

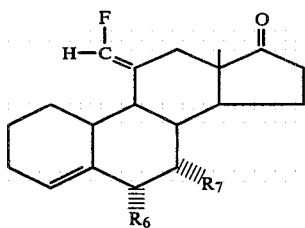

(XII')

where

R₆ is a hydrogen atom or methyl group with the proviso that when R₆ is a methyl group, R₇ is a hydrogen atom; and R₇ is a hydrogen atom or methyl group with the proviso that when R₇ is a methyl group, R₆ is a hydrogen atom.

6. A (E)-11-fluoromethylene steroid according to claim 5 which is selected from the group consisting of (E)-11-(fluoromethylene)estr-4-ene-3,17-dione, (E)-11-fluoromethylene-7α-methylestr-4-ene-3,17-dione, (E)-11-(fluoromethylene)estr-4-ene-3,17-dione 3-ethanedithiol ketal, and (E)-11-fluoromethylene-7α-methylestr-4-ene-3,17-dione 3-ethanedithiol ketal.

7. A E-(11)-fluoromethylene steroid selected from the group consisting of a 3-unsubstituted (E)-11-fluoromethylene steroid of the formula

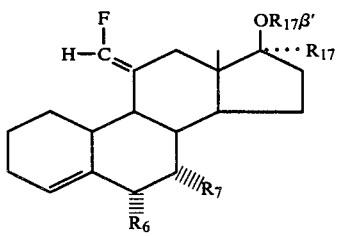

(VII')

a Δ⁴-3-keto(E)-11-fluoromethylene steroid of the formula,

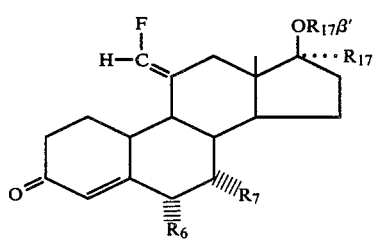

(VIII')

a Δ⁵⁽¹⁰⁾-3-keto-(E)-11-fluoromethylene steroid of the formula,

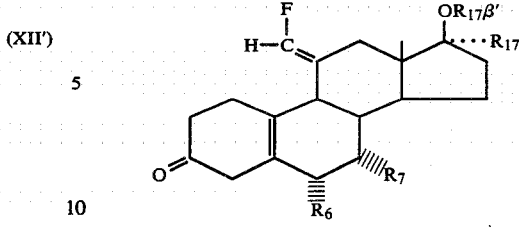

and a Δ⁴,⁹-(E)-11-fluoromethylene steroid of the formula

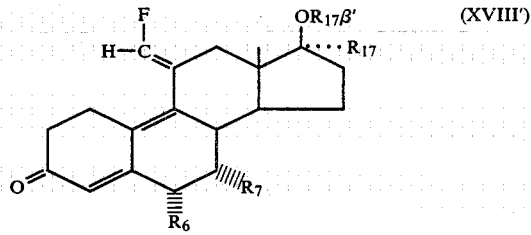

where

R₆ is a hydrogen atom or methyl group with the proviso that when R₆ is a methyl group, R₇ is a hydrogen atom;

R₇ is a hydrogen atom or methyl group with the proviso that when R₇ is a methyl group, R₆ is a hydrogen atom;

R₁₇ is a hydrogen atom, alkyl of 1 through 4 carbon atoms, —C≡C—R₁₇ₐ, —CH=CH—R₁₇ᵦ; and R₁₇ₐ is a hydrogen atom, methyl or ethyl group or trifluoromethyl;

R₁₇ᵦ is a hydrogen atom, methyl or ethyl group or —CH=CH₂ group;

R₁₇β' is a hydrogen atom or R₁₇β;

R₁₇β is alkyl of 1 through 4 carbon atoms and OCO—R₁₇C;

R₁₇C is alkyl of 1 through 6 carbon atoms, cyclopentylethyl and phenyl.

8. A (E)-11-fluoromethylene steroid according to claim 7 where R₁₇ is selected from the group consisting of a hydrogen atom, methyl, ethynyl or propynyl group.

9. A (E)-11-fluoromethylene steroid according to claim 7 where R₁₇β' is selected from the group consisting of a hydrogen atom, methyl or acetyl group.

10. A (E)-11-fluoromethylene steroid according to claim 7 which is selected from the group consisting of 17α-ethynyl-(E)-11-(fluoromethylene)estr-4-ene, 17α-ethynyl-(E)-11-fluoromethylene-17β-hydroxyestr-4-en-3-one, (E)-11-fluoromethylene-17β-hydroxy-17α-propynylestr-4-en-3-one, 17α-ethynyl-(E)-11-fluoromethylene-17α-hydroxy-7α-methylestr-4-en-3-one, (E)-11-fluoromethylene-17β-hydroxy-7α-methyl-17α-propynylestr-4-en-3-one, and (E)-11-fluoromethylene-17β-hydroxy-17α-propynylestr-4-en-3-one 17-methyl ether.

11. A (E)-11-fluoromethylene steroid according to claim 5 which is (E)-11-(fluoromethylene)estr-4-en-17-one.

12. A (E)-11-fluoromethylene steroid according to claim 7 which is selected from the group consisting of (E)-11-fluoromethylene-17β-hydroxy-17α-methylestr-4-en-3-one, (E)-11-fluoromethylene-17β-hydroxyestr-4-en-3-one, (E)-11-fluoromethylene-17β-hydroxyestr-4-en-3-one 17-acetate, (E)-11-fluoromethylene-17β-hydroxy-17α-propynylestr-4-ene and 17α-ethynyl-17β-hydroxy-(E)-11-fluoromethyleneestr-4-ene.

* * * * *

UNITED STATES PATENT OFFICE
CERTIFICATE OF CORRECTION

Patent No. 4,557,867        Dated December 10, 1985

Inventor(s) J. Allan Campbell

It is certified that error appears in the above-identified patent and that said Letters Patent are hereby corrected as shown below:

Title page, line 2, "STERIODS" should read --STEROIDS--.
Column 1, line 3, "STERIODS" should read --STEROIDS--.
Column 14, line 37, "to foam" should read --to a foam--.
Column 23, line 55, (mull) "3428" should read --3438--.
Column 29, line 18, "(CDCl$_3$" should read --(CHCl$_3$--.

Column 30, line 46, "is THF" should read --in THF--.
Column 33, line 9, "hydroxyl" should read --hydroxy--.
Column 35, line 44, Chart B (I) "  should read --  --.

Column 36, lines 14-15, Chart B (Z) "  should read -- 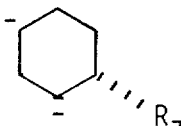 --.

Column 40, line 30, Chart E (XIII), "VIII)" should read --(VII)--.
Column 39, line 66, Chart F (XV), "R$_6$ should read --R$_6$--.

Column 50, line 17, Chart A-Et (A-Et), " 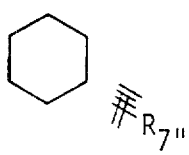 should read -- 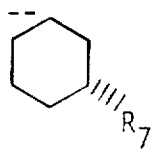 --.

UNITED STATES PATENT OFFICE
CERTIFICATE OF CORRECTION

Patent No. 4,557,867  Dated December 10, 1985

Inventor(s) J. Allan Campbell

It is certified that error appears in the above-identified patent and that said Letters Patent are hereby corrected as shown below:

Column 52, line 10, Chart C-Et (IV-Et), "$F_3HC\diagdown$" should read --$F_2HC\diagdown$--.

Column 52, line 16, "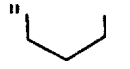" should read ----.

Column 53, line 34, Chart D-Et (VII-Et), "" should read ----.

Column 56, line 65 (I), "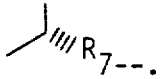" should read ----.

Column 69, line 8, Claim 1 (VII), "" should read ----.

Column 70, line 62 (IV') "" should read ----.

Signed and Sealed this

Twenty-eighth Day of October, 1986

[SEAL]

Attest:

DONALD J. QUIGG

Attesting Officer   Commissioner of Patents and Trademarks